US012673251B2

(12) United States Patent
Andon et al.

(10) Patent No.: US 12,673,251 B2
(45) Date of Patent: Jul. 7, 2026

(54) METHOD OF CONTROLLING OR AUGMENTING A VIRTUAL ENVIRONMENT OR LIVE VIDEO BROADCAST VIA SENSED MOTION

(71) Applicant: NIKE, Inc., Beaverton, OR (US)

(72) Inventors: Christopher Andon, Portland, OR (US); Bobby LeGaye, Portland, OR (US); Hien Tommy Pham, Beaverton, OR (US); Adam Tenuta, Portland, OR (US)

(73) Assignee: NIKE, Inc., Beaverton, OR (US)

( * ) Notice: Subject to any disclaimer, the term of this patent is extended or adjusted under 35 U.S.C. 154(b) by 861 days.

(21) Appl. No.: 17/751,592

(22) Filed: May 23, 2022

(65) Prior Publication Data

US 2022/0279890 A1 Sep. 8, 2022

Related U.S. Application Data

(63) Continuation of application No. PCT/US2020/061884, filed on Nov. 23, 2020.

(Continued)

(51) Int. Cl.
*A63B 24/00* (2006.01)
*A43B 3/36* (2022.01)
(Continued)

(52) U.S. Cl.
CPC ............ *A63B 71/0605* (2013.01); *A43B 3/36* (2022.01); *A43B 3/44* (2022.01); *A43B 3/48* (2022.01);
(Continued)

(58) Field of Classification Search
CPC .... A61B 5/1118; A61B 5/1114; A61B 5/1116; A61B 5/1123; A61B 5/7405;
(Continued)

(56) References Cited

U.S. PATENT DOCUMENTS 5,461,188 A 10/1995 Drago et al.
6,043,891 A 3/2000 Hartrumpf et al.
(Continued)

FOREIGN PATENT DOCUMENTS

CN 101454812 A 6/2009
CN 101645775 A 2/2010
(Continued)

*Primary Examiner* — Yingchun He
(74) *Attorney, Agent, or Firm* — Quinn IP Law

(57) ABSTRACT

A method of controlling or augmenting a virtual environment or a live video broadcast according includes receiving a data stream that is indicative of a monitored spatial motion of an article of footwear or apparel worn by a subject. The data stream is generated at least in part by an accelerometer or inertial measurement unit provided on the article of footwear or apparel. The method further includes identifying at least one motion primitive from the received data stream, augmenting the virtual reality (VR) environment or the live video broadcast with a visual effect in response to the identified motion primitive, and transmitting a view of the VR environment or the live video broadcast to a user for display on a display device.

11 Claims, 17 Drawing Sheets

Related U.S. Application Data

(60) Provisional application No. 63/032,689, filed on May 31, 2020, provisional application No. 62/939,309, filed on Nov. 22, 2019.

(51) Int. Cl.

| | |
|---|---|
| *A43B 3/44* | (2022.01) |
| *A43B 3/48* | (2022.01) |
| *A43B 3/50* | (2022.01) |
| *A61B 5/11* | (2006.01) |
| *A63B 71/06* | (2006.01) |
| *G06F 3/01* | (2006.01) |
| *G06F 16/635* | (2019.01) |
| *G06F 16/683* | (2019.01) |
| *G06F 16/738* | (2019.01) |
| *G06F 16/783* | (2019.01) |
| *G06Q 30/0207* | (2023.01) |
| *G06T 13/00* | (2011.01) |

(52) U.S. Cl.
CPC .............. *A43B 3/50* (2022.01); *A61B 5/1118* (2013.01); *A63B 24/0006* (2013.01); *A63B 24/0021* (2013.01); *A63B 71/0622* (2013.01); *A63B 71/0669* (2013.01); *G06F 3/011* (2013.01); *G06F 3/017* (2013.01); *G06F 16/635* (2019.01); *G06F 16/683* (2019.01); *G06F 16/739* (2019.01); *G06F 16/786* (2019.01); *G06Q 30/0209* (2013.01); *A63B 2024/0012* (2013.01); *A63B 2024/0025* (2013.01); *A63B 2071/0625* (2013.01); *A63B 2220/40* (2013.01); *A63B 2220/833* (2013.01); *A63B 2225/20* (2013.01); *A63B 2225/50* (2013.01); *A63B 2225/74* (2020.08); *A63B 2244/22* (2013.01); *G06T 13/00* (2013.01)

(58) Field of Classification Search
CPC ..... A61B 5/744; A61B 5/7455; A61B 5/6807; A61B 2503/12; A61B 2503/0219; A63B 71/0605; A63B 71/0622; A63B 71/0669; A63B 24/0006; A63B 24/0021; A63B 2024/0012; A63B 2024/0025; A63B 2071/0625; A63B 2220/40; A63B 2220/833; A63B 2220/20; A63B 2220/50; A63B 2220/74; A63B 2244/22; A43B 3/36; A43B 3/44; A43B 3/48; A43B 3/50; A43B 3/38; A43B 3/34; G06F 3/011; G06F 3/017; G06F 3/0346; G06F 16/635; G06F 16/683; G06F 16/739; G06F 16/786; G06F 1/1694; G06F 1/163; G06Q 30/0209; G06T 13/00; A43C 11/165; A63F 13/235; A63F 13/812; A63F 13/816; A63F 13/211; A63F 13/212; A63F 13/285; A63F 13/352; A63F 13/428; A63F 13/46; A63F 13/54; G10H 2220/326; G10H 2220/336; G10H 2220/395; H04N 21/234; H04N 21/235; H04N 21/42202; H04N 21/462
See application file for complete search history.

(56) References Cited

U.S. PATENT DOCUMENTS

| | | | |
|---|---|---|---|
| 7,207,688 B2 | 4/2007 | Yuen et al. |
| 7,494,237 B1 | 2/2009 | Cheung |
| 8,056,269 B2 | 11/2011 | Beers et al. |
| 8,099,258 B2 | 1/2012 | Alten et al. |
| 8,356,430 B2 | 1/2013 | Beers |
| 8,813,395 B2 | 8/2014 | Beers et al. |
| 8,919,982 B2 | 12/2014 | Pulido, Jr. |
| 9,282,893 B2 | 3/2016 | Longinotti-Buitoni et al. |
| 9,365,387 B2 | 6/2016 | Beers et al. |
| 10,004,291 B2 | 6/2018 | Beers et al. |
| 10,182,608 B2 | 1/2019 | Smith et al. |
| 10,423,241 B1 | 9/2019 | Pham et al. |
| 10,448,707 B2 | 10/2019 | Walker et al. |
| 11,176,854 B2 | 11/2021 | Tseng |
| 2007/0041193 A1 | 2/2007 | Wong et al. |
| 2008/0203144 A1 | 8/2008 | Kim |
| 2009/0158622 A1 | 6/2009 | Cook et al. |
| 2010/0035688 A1 | 2/2010 | Picunko |
| 2011/0025524 A1 | 2/2011 | Lee et al. |
| 2012/0029994 A1 | 2/2012 | Barkan et al. |
| 2012/0078393 A1 | 3/2012 | Kotb et al. |
| 2012/0297960 A1 | 11/2012 | Bader |
| 2013/0095926 A1 | 4/2013 | Trewartha et al. |
| 2013/0288761 A1 | 10/2013 | Santos Paiva Ferraz Conceicao |
| 2014/0070957 A1 | 3/2014 | Longinotti-Buitoni et al. |
| 2014/0376876 A1* | 12/2014 | Bentley .................. G06V 40/23 386/227 |
| 2015/0181314 A1 | 6/2015 | Swanson |
| 2015/0370320 A1 | 12/2015 | Connor |
| 2016/0027209 A1* | 1/2016 | Demirli ................. G06T 19/003 345/419 |
| 2016/0322078 A1 | 11/2016 | Bose et al. |
| 2016/0324445 A1 | 11/2016 | Kim et al. |
| 2016/0338644 A1* | 11/2016 | Connor ................ A61B 5/1126 |
| 2016/0346612 A1 | 12/2016 | Rowley |
| 2017/0095181 A1 | 4/2017 | Hauenstein et al. |
| 2017/0150773 A1 | 6/2017 | Beers |
| 2017/0177091 A1 | 6/2017 | Shah et al. |
| 2017/0265583 A1 | 9/2017 | Schneider et al. |
| 2017/0340984 A1 | 11/2017 | Lee |
| 2017/0370320 A1 | 12/2017 | Idogawa |
| 2018/0060943 A1 | 3/2018 | Mattingly et al. |
| 2018/0199657 A1 | 7/2018 | Kikukawa |
| 2018/0199673 A1 | 7/2018 | Schneider et al. |
| 2018/0214777 A1 | 8/2018 | Hingorani |
| 2018/0301057 A1* | 10/2018 | Hargrove ............ A61B 5/6824 |
| 2019/0028803 A1 | 1/2019 | Benattar |
| 2019/0059461 A1 | 2/2019 | Walker |
| 2019/0200690 A1 | 7/2019 | Carbo, Jr. et al. |
| 2019/0213619 A1 | 7/2019 | Andon et al. |
| 2019/0266404 A1 | 8/2019 | Spivack et al. |
| 2020/0001812 A1* | 1/2020 | Cho ...................... G06F 3/0304 |
| 2020/0170331 A1 | 6/2020 | Donohoe |
| 2020/0184547 A1 | 6/2020 | Andon et al. |
| 2020/0215390 A1 | 7/2020 | Shin |
| 2020/0273048 A1 | 8/2020 | Andon et al. |
| 2020/0297063 A1 | 9/2020 | Andon et al. |
| 2021/0026440 A1 | 1/2021 | Poupyrev et al. |
| 2021/0161441 A1 | 6/2021 | Waltman et al. |
| 2021/0243031 A1 | 8/2021 | Pegoraro |

FOREIGN PATENT DOCUMENTS

| | | |
|---|---|---|
| CN | 208837163 U | 5/2019 |
| EP | 1729615 A2 | 12/2006 |
| EP | 2783630 A1 | 10/2014 |
| JP | 2004503888 A | 2/2004 |
| JP | 2006114174 A | 4/2006 |
| JP | 5819856 B2 | 11/2015 |
| JP | 5847831 B2 | 1/2016 |
| JP | 2016052368 A | 4/2016 |
| JP | 2016538655 A | 12/2016 |
| JP | 2017521017 A | 7/2017 |
| JP | 2018005375 A | 1/2018 |
| JP | 2018007828 A | 1/2018 |
| JP | 2018094326 A | 6/2018 |
| JP | 2018191760 A | 12/2018 |
| JP | 6481057 B1 | 3/2019 |
| JP | 2019054900 A | 4/2019 |
| JP | 6514397 B1 | 5/2019 |
| JP | 6526898 B1 | 6/2019 |
| JP | 6603734 B2 | 11/2019 |
| JP | 2020503540 A | 1/2020 |
| KR | 20020043016 A | 6/2002 |

(56) References Cited

FOREIGN PATENT DOCUMENTS

| | | |
|---|---|---|
| KR | 20120075858 A | 7/2012 |
| KR | 101936417 B1 | 1/2019 |
| KR | 20190110566 A | 9/2019 |
| KR | 20190111936 A | 10/2019 |
| WO | 2016111069 A1 | 10/2017 |

* cited by examiner

METHOD OF CONTROLLING OR AUGMENTING A VIRTUAL ENVIRONMENT OR LIVE VIDEO BROADCAST VIA SENSED MOTION

CROSS-REFERENCE TO RELATED APPLICATIONS

The present application is a continuation of International Patent Application No. PCT/US2020/061884, filed Nov. 23, 2020, which claims the benefit of priority from U.S. Provisional Patent Application Nos. 62/939,309, filed 22 Nov. 2019, and 63/032,689, filed 31 May 2020, and all of which are incorporated by reference in their entirety.

TECHNICAL FIELD

The present disclosure relates to a system for analyzing a user's real time motion via instrumentation provided in a worn article of footwear or apparel.

BACKGROUND

In both the exercise world and in connections with movement-based social media challenges, users are often asked or challenged to perform a series of dynamic movements or a choreographed dance in time with a beat or musical sample. While performing these challenges is sometimes a feat in itself, performing these challenges completely, correctly, and fluidly from movement to movement is where the real challenge lies. Without a coach standing nearby, it is difficult for an individual to truly understand how their performance compares to some idealized standard.

SUMMARY

The present disclosure relates to a system that may sense and process a user's real time spatial motion via instrumentation provided in a worn article of footwear or apparel. This motion may then be compared to an idealized standard, to the motion of a friend or other user to better understand how accurately and completely their motions track. This correspondence may be converted into an accuracy metric, which may be shared with the user, a coach, or a broader community over a distributed computing network.

In addition to purely scoring the user's motions, the present system may also add an element of creative multimedia expression, where the user's motions are operative to trigger the output of one or more audio samples or visual effects. In this manner, the user may feel or express their motions via other sensory outputs.

Additional benefits and aspects of this disclosure are provided in the following disclosure.

DETAILED DESCRIPTION

Figure 1:
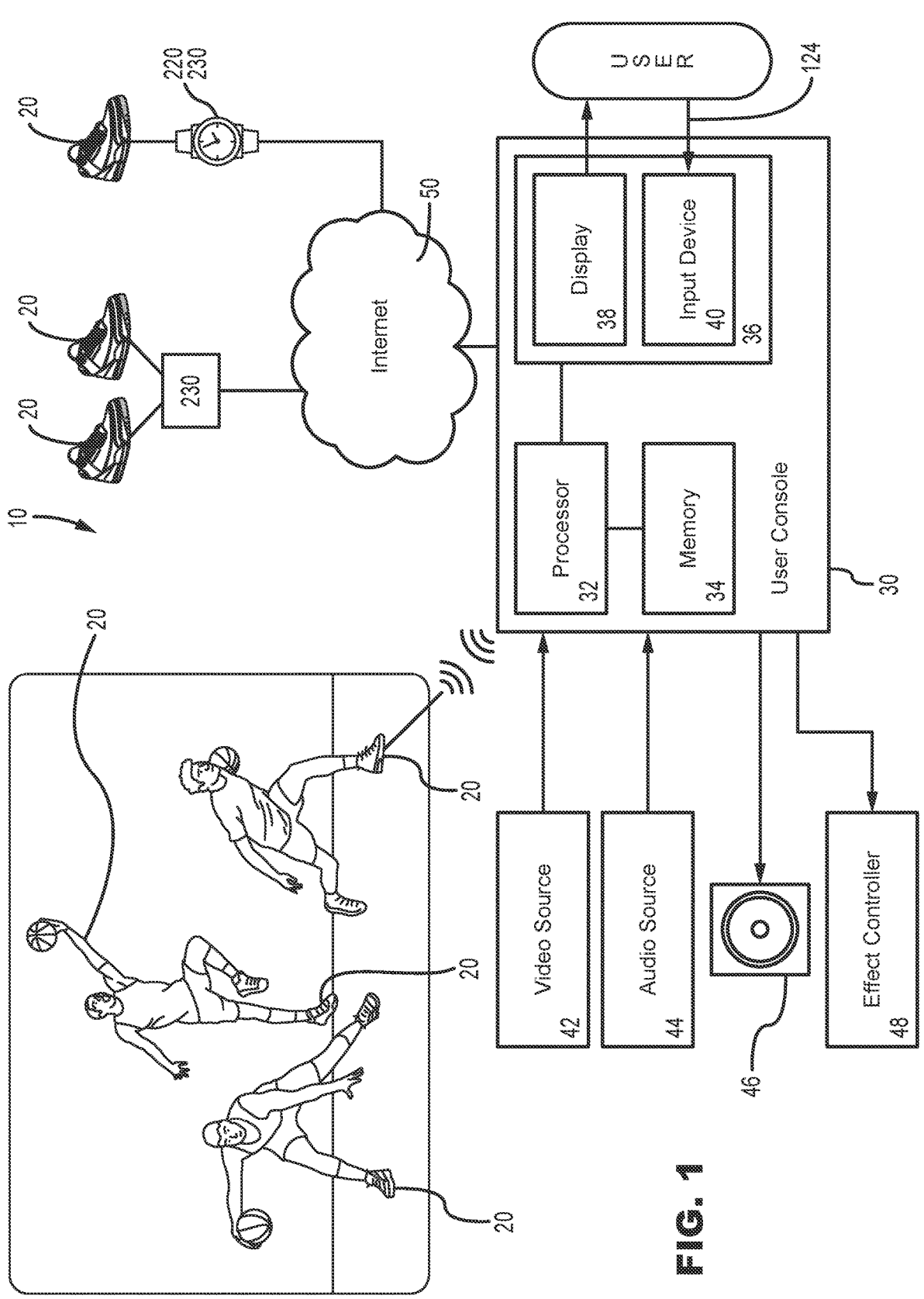
FIG. 1 is a schematic illustration of an embodiment of a system for motion-based media creation.

The following discussion and accompanying figures disclose a system that uses directly sensed body motion to trigger the playback of one or more audio samples or visual effects. This technology is intended to create a new form of expression, whereby the movement of a dancer or athlete can drive the creation of an electronic multimedia experience.

In addition to simply providing the tools to compose an audio/visual (A/V) experience, some embodiments of the present technology may enable a social collaboration between a plurality of users. For example, in some configurations, multiple users of the system may collaborate in a local or networked manner to make joint/collaborative A/V compositions. In another example, multiple networked users may issue and/or respond to motion-based challenges from each other.

In a collaborative context, some embodiments of the present technology may enable multiple members of a dance troupe or social network to collaborate in the creation of an A/V composition, much in the same way a symphony performs. In particular, each user or small group of users may have unique sounds or visual effects associated with their movement. During the performance, the combined sound output resulting from each member's movement may produce a performance-based A/V composition where the various user's bodies become the "instruments."

Regarding challenges in a social media context, it has become increasingly popular for individuals to make online challenges to each other via various social media platforms. These challenges often involve users performing one or more actions or dancing to a specific audio clip. One example of such a challenge involved users videotaping themselves dumping icy water on their head and then issuing the same challenge to another user. Other challenges involve performing specific or improvised dance sequences to a portion of a song. In each instance, users may videotape themselves performing the dance/action and post the resulting video clip to an online video hosting service. Examples of such hosting services include TIKTOK and DOUYIN, both operated by Beijing ByteDance Technology Co Ltd., or YOUTUBE, which is operated by Youtube, LLC, a subsidiary of Google, LLC. As will be described below, the present technology may be well suited for similar "challenges."

In some embodiments, the output of the user's expression may exist solely within a separate medium and/or solely for the consumption by others (i.e., "viewers") who are remote to the user. For example, the user's motions may be used to trigger one or more audio and/or visual effects within a virtual environment, such as may exist within a video game. Alternatively, the effects may be presented in an augmented reality (AR) environment, where they may be overlaid on a natural perception of the real world. In such an AR context, the effects may either be delivered to a user device of a person live to the event such that they may be superposed on the user's real world view—as with AR display glasses. Alternatively, the effects may be overlaid on a captured video feed, such as a streamed video (internet or television) broadcast, which may be viewed by a user device such as a mobile phone or television.

As schematically illustrated in FIG. 1, a system for motion-based media creation 10 may generally include an electronic, motion-sensing article of footwear or apparel 20 that is in networked communication with a user console 30. For the purpose of this disclosure, the "electronic, motion-sensing article of footwear or apparel 20" may generally be referred to as a "wearable 20." Each wearable 20 may be styled similar to traditional articles of footwear or apparel, though may have additional electronic functionality to permit the detection and outward transmission of motion data. Examples of suitable articles of footwear may include shoes, boots, sandals, cleated footwear, or the like. Similarly, examples of suitable articles of apparel may include shirts, jackets, pants, shorts, socks, compression sleeves, gloves, hats, arm bands/bracelets, and the like.

Figure 2:
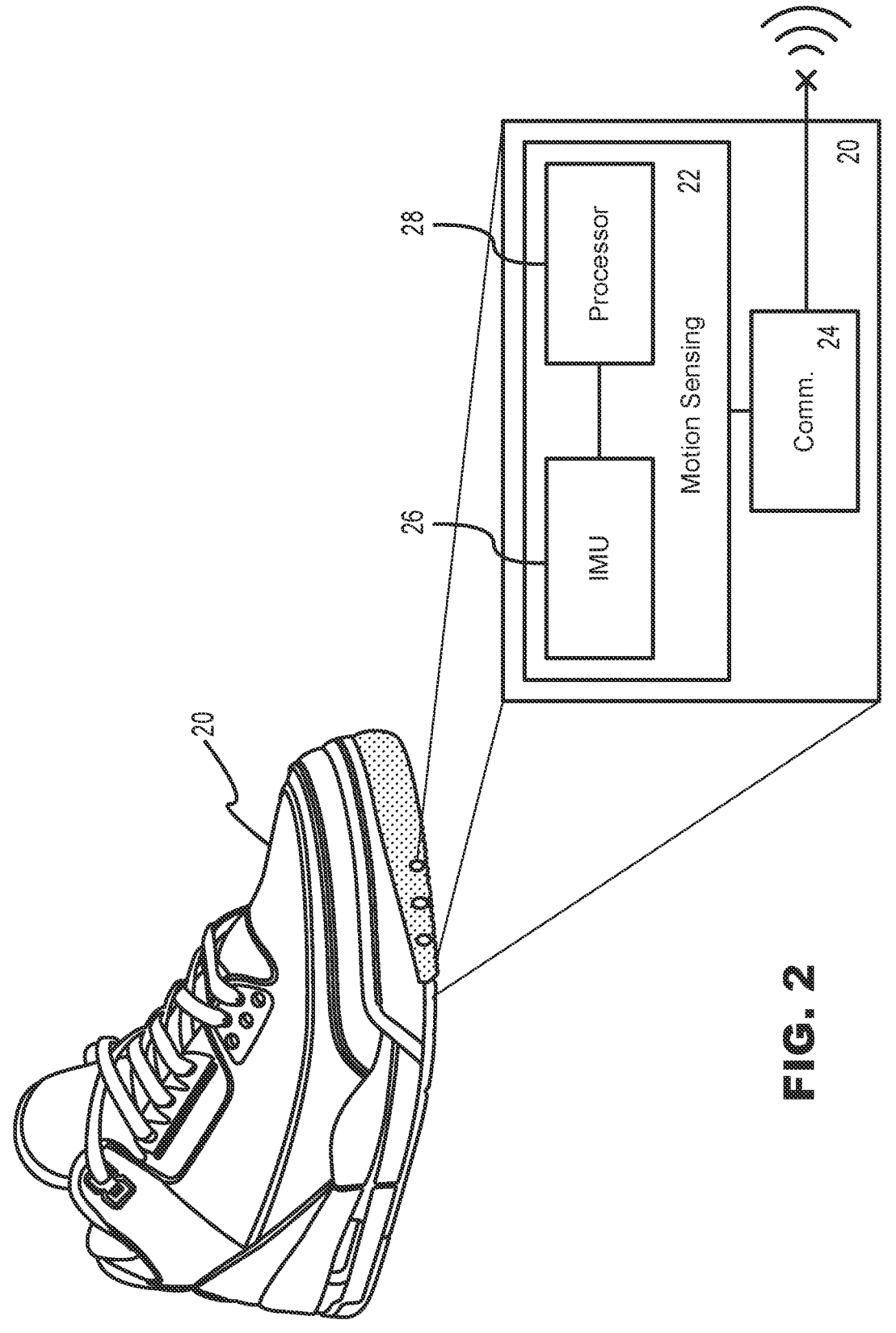
FIG. 2 is a schematic diagram of an electronic, motion-sensing article of footwear.

In the present technology, such as shown in FIG. 2, the wearable 20 may include both a motion sensing circuit 22 and communication circuitry 24. The motion sensing circuit 22 may include at least one accelerometer or inertial measurement unit (IMU) 26 that is operative to sense the spatial motion of at least a portion of the wearable 20 and to generate a data output stream representative of the sensed motion. In some embodiments, the motion sensing circuit 22 may further include a processor 28, memory, and/or any buffering or filtering circuitry that may be required to prepare the data output stream for transmission and/or to convert the raw data output into a streaming sequence of recognized motion primitives (discussed in greater detail below).

The communications circuitry 24 coupled with the motion sensing circuit 22 is configured to outwardly transmit the data stream to the user console 30. The communications circuitry 24 may include one or more transceivers, antenna, and/or memory that may be required to facilitate the data transmission in real time or near real time. This data transmission may occur according to any suitable wireless standard, however particularly suited communication protocols include those according to any of the following standards or industry recognized protocols: IEEE 802.11, 802.15, 1914.1, 1914.3; BLUETOOTH or BLUETOOTH LOW ENERGY (or other similar protocols/standards set by the Bluetooth SIG); 4G LTE cellular, 5G, 5G NR; or similar wireless data communication protocols.

Referring again to FIG. 1, the user console 30 in communication with the wearable 20 may comprise a computing device operating software or firmware that is specifically designed to cause the computing device to perform as described below. The user console may include a processor 32, memory 34, and user interface 36. In general, the processor 32 used with the present system 10 may be embodied as one or multiple digital computers, data processing devices, and/or digital signal processors (DSPs), which may have one or more microcontrollers or central processing units (CPUs), read only memory (ROM), random access memory (RAM), electrically-erasable programmable read only memory (EEPROM), a high-speed clock, analog-to-digital (A/D) circuitry, digital-to-analog (D/A) circuitry, input/output (I/O) circuitry, and/or signal conditioning and buffering electronics. Examples of suitable user consoles include smart phones, tablet computers, laptop computers, desktop computers, and the like.

The user interface 36 may be configured to provide the user with the ability to view and/or hear available A/V effects while also enabling the user to build out a correspondence table. In some embodiments, the user interface 36 may include one or more displays 38 operative to output visual information to a user and/or one or more user input devices 40 operative to receive an input from the user. Examples of user input devices 40 include a touch screen/digitizer, a mouse, a keyboard, and/or a control panel having a plurality of rotary knobs and/or buttons, a camera, a gesture-based input device, AR/VR virtual selection, etc..

With continued reference to FIG. 1, in addition to being in communication with the wearable 20, in some embodiments, the user console 30 may also be in communication with one or more video sources 42, one or more audio sources 44, one or more audio output devices 46, one or more visual effect controllers 48, and/or a distributed computing network 50 (e.g., the Internet). The video sources 42 may include live video streams (e.g., from a digital camera), previously recorded video streams, digital memory storing one or more previously recorded videos, and the like. The audio sources 44 may include one or more musical instruments, keyboards, synthesizers, data files, collections of audio samples, and the like. In some embodiments, the video sources 42 and/or audio sources 44 may be local to the user console 30 or provided on a common local area network (LAN). In other embodiments, however, one or both of these sources 42, 44 may be remote from the user console 30 and/or may be hosted by a computer that is accessible only though the console's network connection.

The one or more audio output devices 46 may include one or more speakers, amplifiers, headphones, or other devices operable to broadcast audible sound in response to a received digital or analog audio signal. It is through these audio output devices 46 that the user console 30 will output one or more audio samples in response to the sensed movement. The visual effect controllers 48 may include one or more devices operable to illuminate one or more lights, initiate one or more lighting sequences, initiate one or more pyrotechnic effects, or the like. In some embodiments, a visual effect controller 48 may be resident on the wearable 20, such as to drive an LED or fiber optic visual illumination. Examples of such implementations are described in further detail below.

Figure 3:
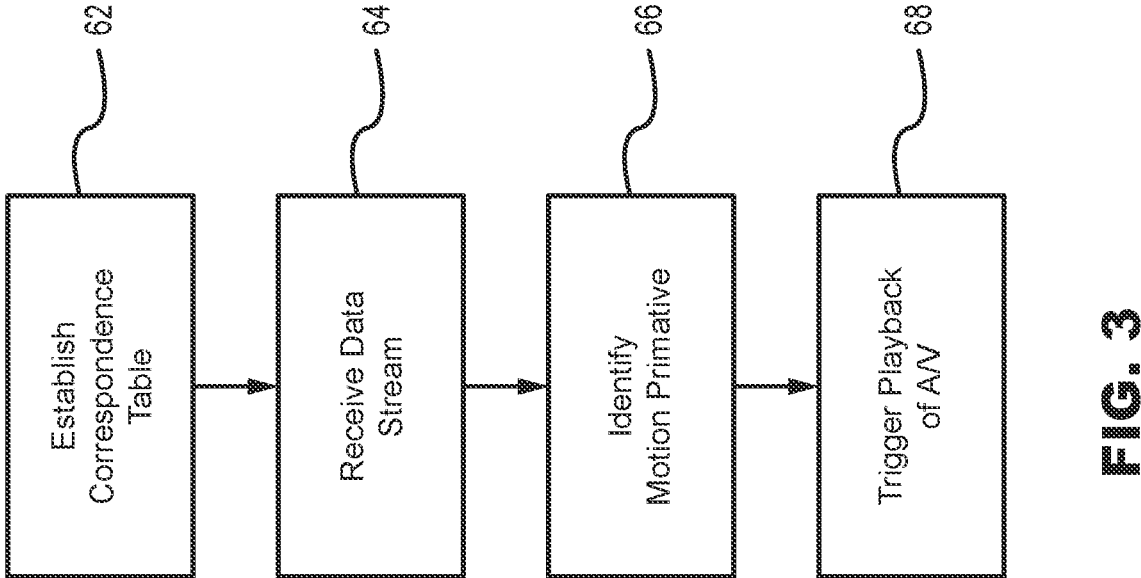
FIG. 3 is a schematic flow diagram of a method of operation for a system of motion-based media creation.

In operation, the user console 30 may serve to translate one or more sensed motions (i.e., of the wearable 20) into one or more audio or visual effects. By chaining various motions together, the user may be able to "play" a sequence of sounds or visual effects. FIG. 3 schematically illustrates a method of operation for the present system 10 from the perspective of the user console 30. As shown, the method begins by establishing a motion correspondence table (at 62) that correlates sensed motion with a desired audio/visual response. This step is largely an initialization step, and in some embodiments, may be performed solely by loading a pre-established motion correspondence table into memory.

Once a motion correspondence table is established, the console 30 may receive a data stream from the article of footwear or apparel (at 64) that is indicative of the motion of the wearable. The user console 30 may continuously analyze this data stream in an effort to identify at least one motion primitive (at 66). As used herein, a "motion primitive" is a defined "block" of motion representing a discrete user action. Examples of possible motion primitives may include sensed linear translation, arcuate translation, sinusoidal/periodic translation, rotation, acceleration, jerk, and/or impact. In a general sense, motion primitives may include any combination of pre-programmed motions, user defined motions, and/or auto detected motions.

If one or more motion primitives are recognized from the data stream (at 66), the console 30 may trigger the playback (at 68) of an audio sample or visual effect that has been previously associated with that motion primitive. In some embodiments, the audio sample or visual effect that has been previously associated with that motion primitive may be a sequence of audio samples or visual effects, or a repeating sequence of audio samples or video effects. For example, upon detection of a user stomping their foot (e.g., a motion primitive characterized by a downward velocity followed by a sudden deceleration), the user console 30 may trigger the playback of a single bass beat. Alternatively, it may trigger the playback of a plurality of bass beats, and/or may trigger the playback of a looped sequence of bass beats. In this manner, the system provides extreme flexibility for the user to define what audio or video effect each movement (or sequence of movements) may cause/initiate.

Figure 4:
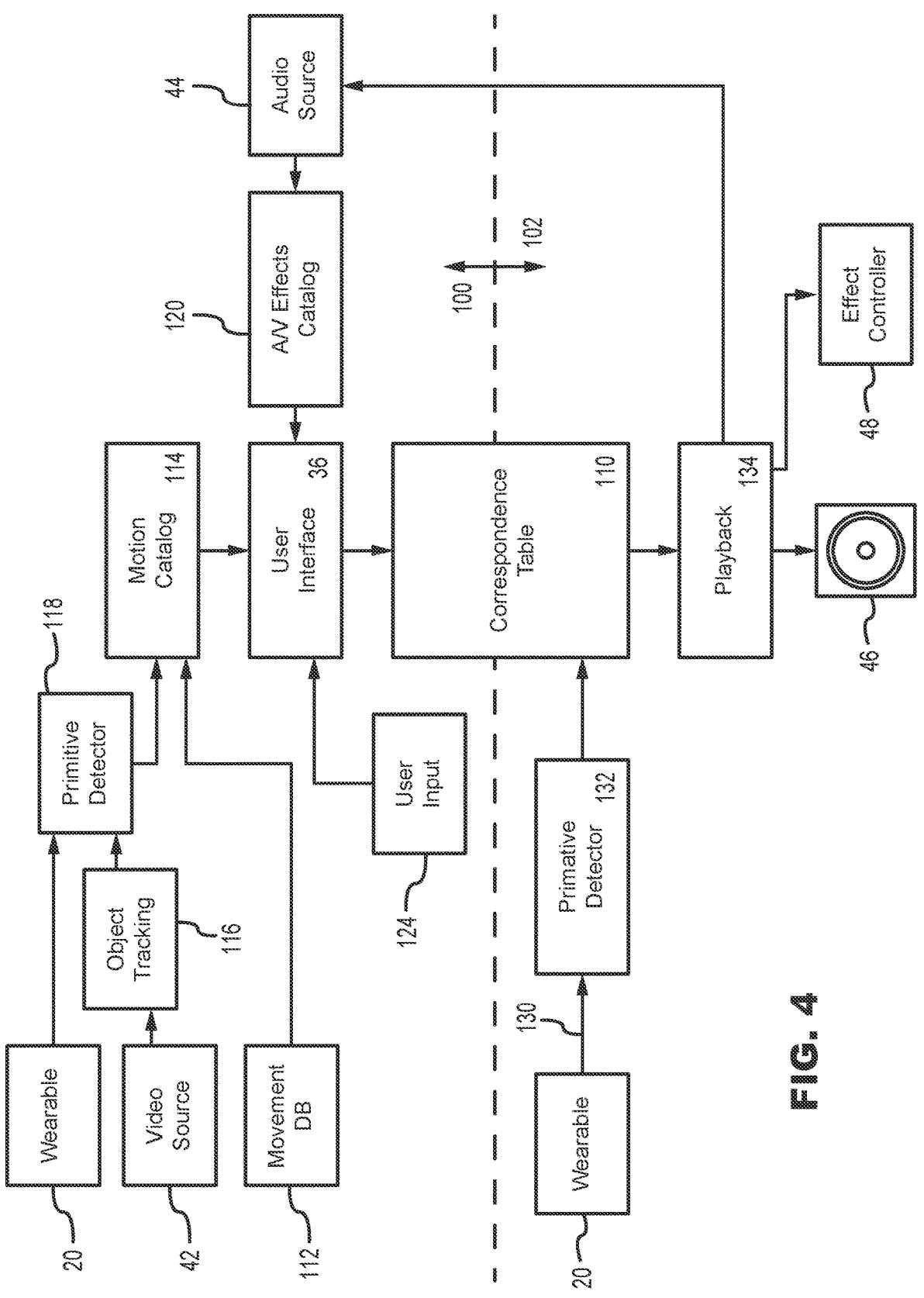
FIG. 4 is a schematic functional block diagram of the operation of a system for motion-based media creation.

FIG. 4 schematically illustrates a functional block diagram of the operation of the present system. Each of the described modules or blocks may comprise computer executable code, stored in memory as software or firmware, such that when executed, the processor 32 may perform the specified functions. In some embodiments, each block may further include any or all requisite hardware that may be required or may be beneficially used to perform the specified functions. Examples of such hardware can include video or audio encoders/decoders, digital signal processors (DSP), and the like.

Referring to FIG. 4, the system operation may generally include two different modes: initialization 100, and media generation 102. During initialization 100, the processor 32 may be tasked with establishing a motion correspondence table 110 that correlates sensed motion with a desired audio/video response. For this purpose, the processor 32 may be in communication with at least one of a pre-existing movement database 112, a video source 42, or a motion-tracking wearable 20. Before building the motion correspondence table 110, the processor 32 may first compile a motion catalog 114 of available or expected motions that may be available for later recognition and playback.

In the simplest embodiment, the motion catalog 114 may simply be imported from a pre-existing movement database 112, which may identify typical or common movements within dance sequences, sports, activities, and the like. If a generic movement database would prove too unwieldy (i.e., too many inapplicable movement options) or not specific enough to the desired activity or dance, then, in some embodiments, the processor 32 may be capable of building out the motion catalog either by parsing movements of a connected wearable 20 (i.e., via a received data stream), or by extracting movement information from a supplied video source 42.

In an embodiment where movement information is extracted from a video, the video source 42 may include, for example, a live and locally captured video, a pre-recorded video, and/or a networked or internet video feed/stream. The video source 42 may be passed through an object recognition and tracking module 116 to recognize and estimate the three-dimensional motion of a depicted wearable (or portion of an individual's body). In one embodiment, the object recognition and tracking module 116 may utilize image processing techniques such as boundary/edge detection, pattern recognition, and/or machine learning techniques to recognize the wearable 20 and to gauge its movement relative to its environment or in a more object-centered coordinate system.

Once either the processor 32 has received the raw data stream from the wearable 20 or has recognized the motion of the depicted wearable from video stream, it may then pass the raw motion through a primitive detection module 118. In this module, the processor 32 may examine the raw motion for one or more motion primitives or sequences of primitives. For each new primitive or sequence detected, the processor 32 may catalog a new general motion or motion type, a new specific motion, or a new motion sequence in the motion catalog 114. A general motion or motion type may be, for example, a translation (e.g., any translation) or an impact. A specific motion may, for example, be a specific translation of the wearable 20 in a particular direction (e.g., a translation of an article of footwear in a medial direction or an impact of a left foot). Finally, a motion sequence may be, for example, multiple primitives sequenced together (e.g., translation in a lateral direction followed by translation in a medial direction).

Once the motion catalog 114 is established, either by direct import, active motion sensing, or video analysis and deconstruction, it may then be presented to a user, along with a collection of available audio samples and/or visual effects 120, via an interactive user interface 36. The user interface 36 may receive a user input 124 that is operative to link one or more cataloged motions (i.e., motion types, specific motions, or motion sequences from the motion catalog 114) with one or more audio samples and/or visual effects from the collection of available audio samples and/or visual effects 120. These established relationships between the motions and the audio samples and/or visual effects may then be stored in a correspondence table 110. In effect, the correspondence table 110 may be the translator that converts future movements into sound or light effects. In addition to making a correspondence between motion and sound/light, the correspondence table 110 may further link one or more motion primitives with haptic responses, such that a spectator, if equipped with the proper hardware in mechanical communication with their body, could feel a prescribed response following a certain motion primitive.

In some embodiments, the correspondence table 110 need not be an entirely separate data construct from the motion catalog 114, but instead may simply include a plurality of pointers, each being appended to a different respective motion entry within the motion catalog 114 and referencing a different effect. Additionally, in some embodiments, the correspondence table may further include a set of rules that modify the prescribed output according to, for example, timing considerations such as the rhythm, tempo, or flow, of the motion. In this example, the timing parameters may be employed to alter the pitch, tone, tempo, or speed of the prescribed output (or color, brightness, persistence or timing of a visual output).

Once the correspondence table 110 is created and initialization 100 is complete, the system 10 may then be set to a media generation mode 102. In the media generation mode 102, the processor 32 may be operative to receive a data stream 130 from the wearable 20 that is indicative of real-time sensed motion of at least a portion of the wearable 20. The data stream 130 may be received via communications circuitry associated with the processor 32, and may be made available to the processor in real time or near real time. From this received data stream 130, the processor 32 may analyze the motion with a primitive detector 132 (which may be similar or identical to the primitive detection module 118 used during initialization 100). As with above, the primitive detector 132 may examine the raw motion represented by the data stream 130 and detect one or more motion primitives or sequences of primitives.

In order to minimize processing time, and thus improve the responsiveness of the system 10, the primitive detector 132 may be configured to only look for motion primitives within the data stream 130 that have been previously defined in the motion catalog 114 and/or assigned with an associated audio sample and/or visual effect in the correspondence table 110. Upon detection of a primitive, the processor 32 may consult the correspondence table 110 and then may trigger or initiate the playback 134 of an audio sample or a visual effect in response to the identified at least one motion primitive.

In some embodiments, the collection of available audio samples and/or visual effects 120 may be populated from a pre-existing library that may be supplied with the software, or that may be downloaded from a connected distributed computing network (e.g. the Internet). In one embodiment, however, the user may be capable of populating or adding to the collection, such as by directly uploading one or more audio samples from a connected audio source 44 (e.g., a personal computer, a digital music player, a synthesizer, a keyboard, or the like), or by recording one or more sounds or sound sequences generated by the system 10 as a result of user movements. More particularly, if the user creates a particular beat/rhythm/composition via movement, they may be able to save that created work in the collection 120 for future playback/triggering by a single discrete motion. In this manner, it may be possible to layer different sounds/compositions for increased effect.

In one configuration, the user may have the ability to alter a degree of smoothing or auto-tuning between the various audio/video effects. In this manner, beginner users may be able to create compositions that sound or appear well produced, even if their movements are not 100% complete or in time. Similarly, the wearable 20 may be configured to anticipate motion primitives based on prior motion or preceding motion if the user is behind in their timing. Conversely, more advanced user may lessen the smoothing/auto-tuning to get more direct control over the output. In some embodiments, the smoothing/auto-tuning can use machine learning and artificial intelligence techniques to blend audio/video elements together, which may rely on the interspersing of additional beats, drawing out notes, predicting subsequent movements based on early motion indications, etc.

In one configuration, the user console 30 may be configured to take a previously recorded/produced audio track/song and divide it into a plurality of discrete segments (auto-segmentation). The nature, duration, and/or segmentation of the various segments may be customized or even separately created by the user (manual segmentation/segment modification). The user console 30 may then either automatically assign motion primitives to each segment, or may prompt the user to assign their own motion primitives to each segment. This may amount to choreographing a dance routine to a chosen song. Then, by performing the scripted motions in time, the user (or group of users) may initiate the playback of the song solely through their movements— segment by segment. In one embodiment, instead of having an absolute correspondence table, the correspondence table 110 may be conditional upon other factors. For example, a given motion primitive may initiate the replay of a first audio segment (of a song) if performed between time 00:00:00 and 00:00:10, or if performed as an initial move, however the same motion primitive may initiate the replay of a second audio segment if performed between time 00:01:40 and 00:02:00, or if it is between the $10^{th}$ and $20^{th}$ recognized primitive, or if it follows the recognition of a different primitive or playback of a prescribed audio segment. In a further embodiment, the varying amount of smoothing/auto-tuning may also be applied to this sequential, playback of music segments, whereas the segments may be blended or final notes may be extended to produce an output that flows from one segment to the next without appearing choppy.

In the case of choreographing existing songs, the user console 30 may include a local memory that has the song stored thereon, or the console may be in communication with an internet-based streaming audio source, for example that the user may separately subscribe to.

In addition to simply outputting basic sounds or beats, or outputting segments of a pre-recorded track/song, in some embodiments, the correspondence table may include one or more motion primitives that are linked to audio action/control commands. For example primitives may be used to initiate playback of a full song, initiate playback of the next song in a list, pause the song, rewind the song, alter the beat of the song, alter the tone of the song, alter the volume of the playback, fade in/out, etc. In this manner, a user, through his/her motions may act as a DJ or producer to playback pre-recorded audio from a local or networked source. Further, the audio action/control commands may operate in conjunction with the display of the user console. For example, primitives may be used to scroll through a list (e.g., to find a certain song/track).

For the purpose of any use-case examples described herein, it should be understood that any audio playback may include discrete sounds, collections of sounds, pre-recorded sounds, segments of audio tracks/songs stored on a local memory, full audio tracks/songs stored on a local memory, segments of audio tracks/songs drawn from an internet-based source (i.e., including songs that may be accessed via a subscription-based login), or full tracks/songs drawn from an internet based source, and the like.

As discussed above, and generally shown in FIG. 1, in some embodiments, the system 10 may accommodate multiple users/wearables 20. In such configurations, each wearable 20 is configured to generate and wirelessly transmit a respective data stream 130 to the user console 30 that is indicative of the monitored spatial motion of that device.

Figure 6:
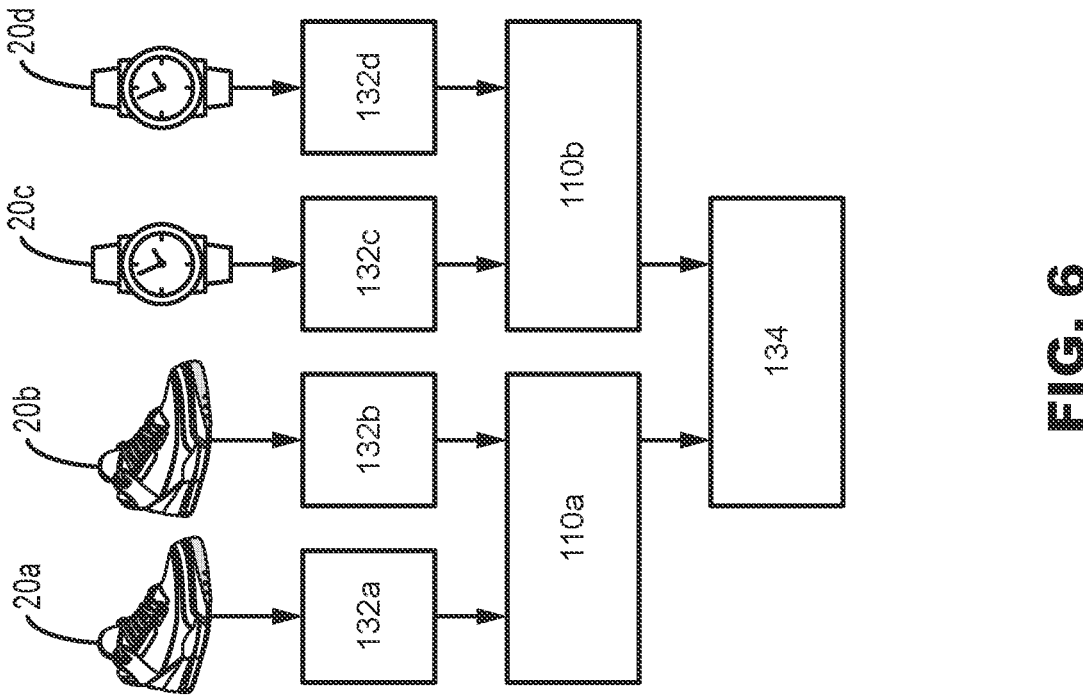
FIG. 6 is a schematic diagram of a plurality of wearables grouped into pods, with each pod having sensed motion of the associated wearables translated into an audio/visual output by a pod-specific set of rules.
Figure 5:
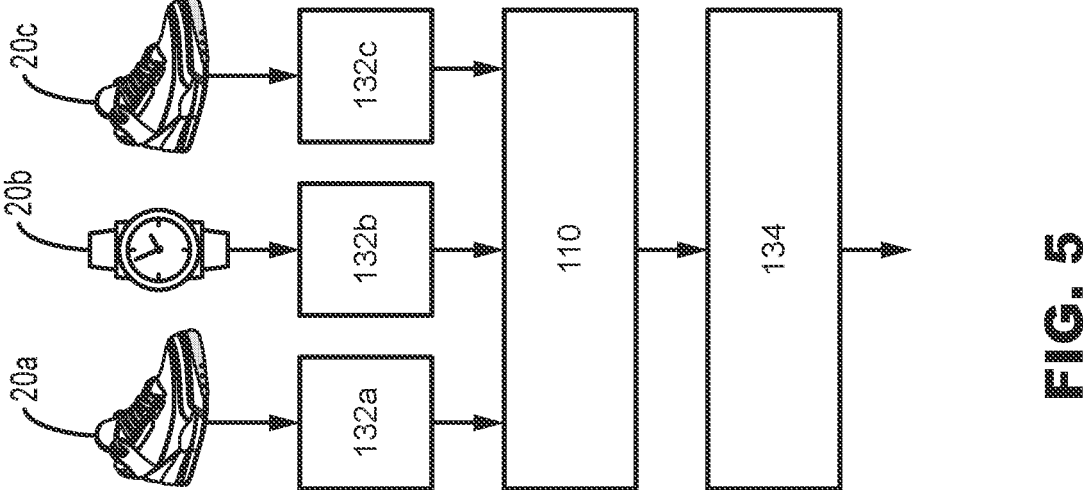
FIG. 5 is a schematic diagram of a plurality of wearables, each having their sensed motion translated into an audio/visual output by a common set of rules.
Figure 7:
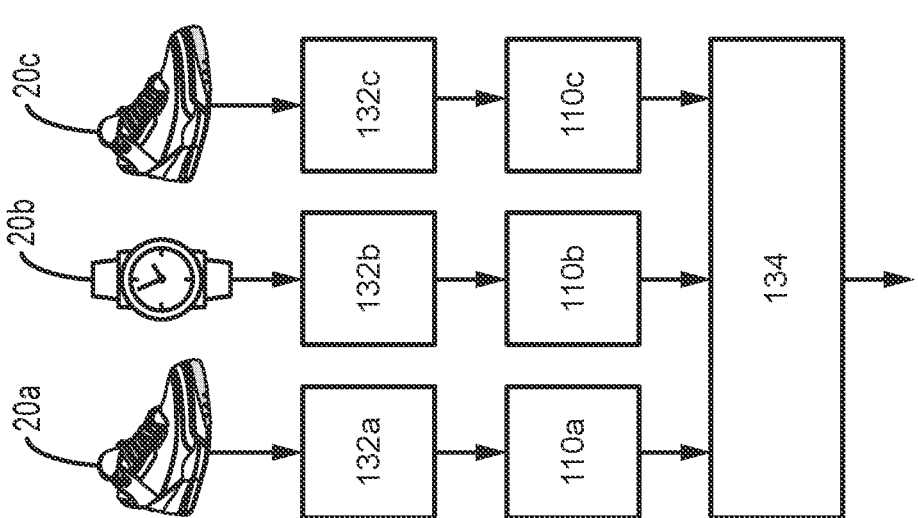
FIG. 7 is a schematic diagram of a plurality of wearables, each having their sensed motion translated into an audio/visual output by a distinct set of rules.

As schematically shown in FIGS. 5-7, the system 10 may be configured so that the correspondence table 110 is globally set for all devices (FIG. 5), is set for groups of devices (FIG. 6), or is set on a device-by-device basis (FIG. 7). If set globally, such as shown in FIG. 5, the console 30 may apply the same set of rules/references for every connected wearable (i.e., wearables 20*a*, 20*b*, and 20*c*). More specifically, the data stream from each wearable 20*a*, 20*b*, 20*c* may be passed through a respective primitive detector 132*a*, 132*b*, 132*c*, which may then reference a common correspondence table 110 before playback at 134. Despite having only a single table, different types of wearables may produce differing sounds by virtue of their differing intended use. For example, it is not likely that a watch would experience the same impact forces that a basketball shoe would.

FIG. 6 illustrates an embodiment where the processor 32 maintains different "pods" of wearables (i.e., wearables 20*a* and 20*b*, and wearables 20*c* and 20*d*) with each pod having its own correspondence table 110*a* and 110*b* (fed by respective primitive detectors 132*a*, 132*b*, 132*c* and 132*d*). In this embodiment, groups of wearables may specialize in their purpose. For example, a first grouping of wearables may cause predominantly bass tones to be output, whereas a second grouping of wearables may cause predominantly piano-like tones or visual effects to be output.

During initialization, different wearables 20 may "subscribe" to a particular pod and thus serve as an input for the A/V linked to that respective pod.

Finally, FIG. 7 schematically illustrates a multi-wearable use where each wearable 20*a*, 20*b*, 20*c* is separately provisioned with its own correspondence table 110*a*, 110*b*, 110*c*. In this multi-wearable environment, motion primitives for each wearable may be assigned separately from motion primitives of other wearables such that similar wearable-specific motions may each result in different outputs. For example, a lateral translation of a connected watch may result in the playback of a first sound (e.g., the impact of a crash cymbal), whereas a similar translation of a connected article of footwear may result in the playback of a second sound (e.g., the impact of a bass drum).

Each of the embodiments illustrated in FIGS. 5-7 provide a system where multiple users can collaborate in creating a common composition. In the embodiment shown in FIG. 5, each wearable is a separate input to a common system. The devices may be capable of creating different motion primitives by virtue of their differing nature and use (e.g., an article of footwear may be capable of different movements than a watch), but ultimately, all motion primitives are fed into the same database for output. A dance troupe may be interested in such a functionality to demonstrate how they move in synchrony (i.e., where out of step movements could result in similar out of step beats). In FIG. 7, much like a small band made up from different instruments, each wearable would be capable of creating a separate suite of sounds/visual effects. In this manner, multiple users may come together to collaborate on a composition, each with their own tone and tenor. Finally, the embodiment shown in FIG. 6 may be similar to a symphony orchestra, where there are groupings of similar instruments, however, each grouping may have a unique tone and tenor. Ultimately, the present technology may be used to create a new artistic expression for motion and may be flexible enough to accommodate both individuals and a collaborative effort.

Referring again to FIG. 1, in other distributed multi-user scenarios, a user's local user console 30 may be in communication, via the distributed computing network 50, with one or more remote user consoles 230 for the purpose of collaboratively interacting or creating a joint audio/visual experience. As such, the physical proximity of devices should not limit the bounds of a user's creativity.

Additionally, it should also be noted that in each embodiment described herein, some or all of the user console may be physically integrated with the wearable 20. For example, in one configuration, the remote user console 230 may not be a separate computing device, but may instead be a smart/connected wearable 220, such as a smart watch. In this embodiment, the smart/connected wearable 220 may include enough processing functionality and communications capabilities to transmit motion data to the distributed network, and may even be able to communicate with one or more audio output devices 46 or visual effect controllers 48 through a communication protocol such as BLUETOOTH. Likewise, the smart/connected wearable 220 may also serve as the user console 30 for one or more other wearables 20 that lack additional processing capabilities.

Building upon this notion of remote users collaborating over a distributed network, in some embodiments, the present system may be utilized in a game-like context whereby users may challenge each other to perform and/or create certain predetermined works of art, or to reproduce certain dance sequences. For example, in one context, a user may be presented with a sequence of movements on a display (e.g., an ordered sequence of motion primitives). Users may then attempt to replicate those movements in time, which if accurately performed, may generate a pre-composed audio or visual output. Deviation in timing or completeness of the user's movements from what was intended/displayed could alter the audible or visual output. Furthermore, in some embodiments, the processor 32 may be configured to determine, from the received the data stream, an accuracy metric that represents a correspondence between the monitored spatial motion of the wearable 20 and the ordered sequence of motion primitives. The accuracy metric may, for example, reflect deviations in timing, magnitude, and/or completeness of the user's motions relative to the presented sequence. In some embodiments, the accuracy metric may be a least squares value between reconstructed spatial curves, in other embodiments, the accuracy metric may include a Frechet distance or some other metric that may represent deviations in ordered multi-dimensional points or curves, in still other embodiments, the accuracy metric may be a composite of a plurality of sub accuracy metrics that account for different aspects of the movement separately (e.g., completeness, acceleration, fluidity, transition, and the like). In some embodiments, the presented sequence may vary in difficulty or complexity based on the experience of the user.

Figure 8:
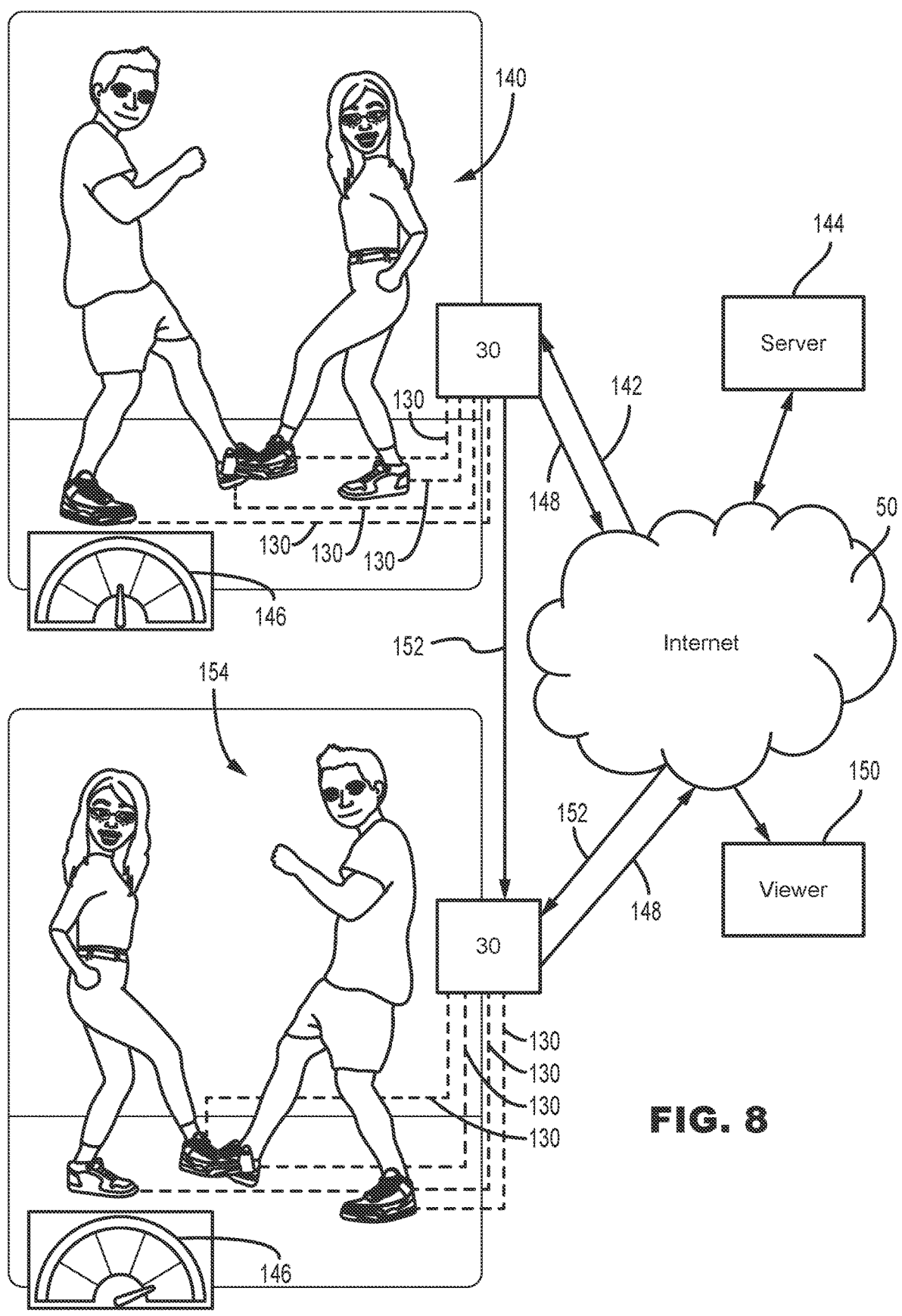
FIG. 8 is a schematic illustration of users performing a motion-based challenge with the present system.

FIG. 8 schematically illustrates one example of such a distributed, challenge-based use. As shown each wearable 20 may be in direct or indirect communication with a distributed computing network 50, such as the internet. The distributed network 50 may comprise one or more servers, computers, routers, switches, and the like that may facilitate network interconnectivity, data aggregation, and/or remote application hosting. In one embodiment of a user challenge, a first user 140 (or grouping of users) may receive, via their user console 30, a sequenced challenge 142 of motions/actions that they are to perform from a remote computing device 144 (which may be part of the distributed computing network 50). Following the receipt of the challenge 142, the first user(s) 140 may attempt to reproduce the ordered sequence of motions, or some variant thereof. Similar to the embodiments described above, each wearable 20 is configured to generate and wirelessly transmit a respective data stream 130 to the user console 30 that is indicative of the monitored spatial motion of that device. From this data stream 130, the user console 130 may generate an associated audio/visual output, and may present the user with qualitative and/or quantitative scoring 146 of their performance (i.e., an accuracy metric 146). The scoring 146 may be computed either by the user console 30, or by the remote computing device 144, and may account for factors such as deviations in timing from a predefined beat, completeness of motions from a predefined magnitude, and/or additional motions that are combined with the base sequence as a means of embellishing the original sequence.

Following completion of a composition or challenge, the user console 30 may transmit an audio or video capture 148 of the composition and/or the accuracy metric/scoring 146 from the challenge to the remote computing device 144, where it may be hosted to be watched by one or more viewers 150 across the distributed network 50. Additionally, the first user 140 may then issue a subsequent challenge 152 to a second user 154 either directly or via the remote computing device 144 and/or distributed network 50.

In another collaborative/competitive example, instead of issuing direct challenges to other users, the present technology may be used to bring physically separated users together and/or gamify a video-based workout streamed over the internet. For example, during an online/streamed kickboxing class, each user watching or listening to the virtual class may be instructed to perform a repeating series of movements or actions. A user's wearable 20 (or the connected user console 30) may sense the motion primitives associated with the user's respective actions, and may cause one or more visual effects to be overlaid onto or displayed on the user's display 38 in conjunction with the instructional video. In one embodiment, the color or nature of the visual effect displayed on the display 38 may be altered according to the similarity, completeness, or timing of the sensed primitive when compared with what is expected or instructed. For example, the user may have green stars appearing or confetti raining down from the top of the display if the user is achieving a new personal best or is above a predefined accuracy threshold. Conversely, the display may provide one or more visual motivators to the user if significant deviation is recognized. In one embodiment, the user's movements may be scored according to the accuracy or completeness of their moves when compared to those of an instructor or idealized reference. This accuracy score may be a moving average of accuracy over a predetermined period of time, and may be displayed on the user's display 38 for personal reference/goal setting. In a situation where a plurality of users are distributed over a network and each watching the video, each user's accuracy score could be broadcast to the collective group (possibly anonymously) so that each user may know where he or she ranks. Likewise, the user's accuracy score may be displayed on the display 38 along with a score of a known influencer, professional athlete, or friend on a social network.

Figure 9:
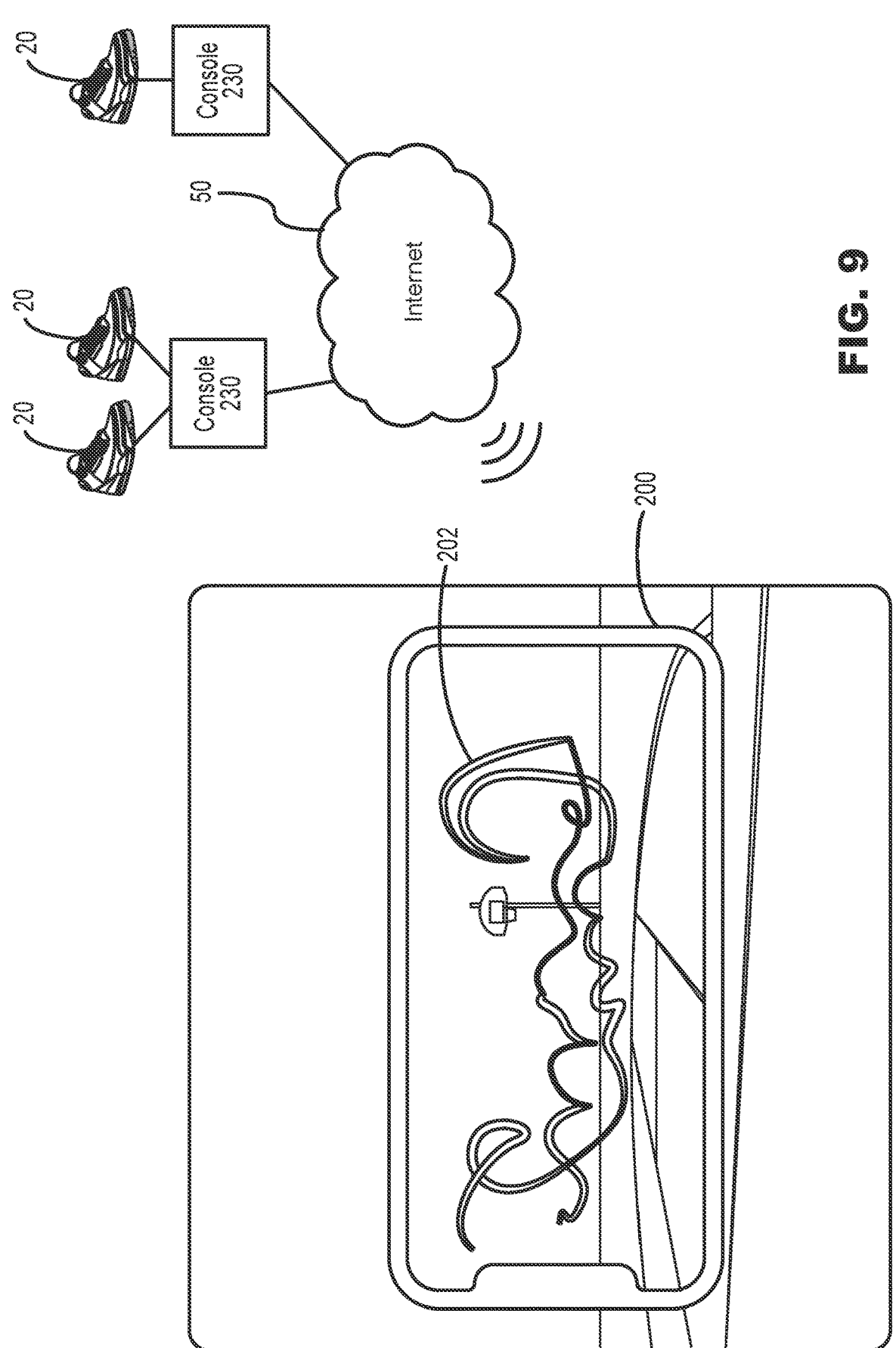
FIG. 9 is a schematic illustration of a user device displaying an augmented reality visual effect resulting from sensed movement of a connected wearable.

Referring to FIG. 9, in some embodiments, spatial movements of one or more wearables 20 may be recorded and uploaded to a cloud-based distributed computing network 50 or remote computing device 144 by one or more user consoles 30, 230. In some embodiments, the visual effect controller 48 may associate one or more visual parameters with the recorded spatial motion such that the motion may be replayed or viewed through an augmented reality-capable device 200. In such an example, the nature of the overlaid AR effect (color, perception of a trace, sequence of visual effects), may be a product of the type of motion primitive that occurred while the spatial motion took place. The augmented-reality capable device 200 may be a smart phone or AR glasses that are operative to overlay a graphical image on a user's real world view (i.e., as perceived through the device), such that the imagery is perceived by the user to exist at a specific real world position.

As shown in FIG. 9, in one embodiment, the spatial movements of one or more wearables may be represented by one or more persistent or time-decaying visual traces 202 that are superimposed upon a displayed real-world image. The visual traces 202 may, for example, represent all or some of the motion on a basketball court throughout a half, a game, or a day. In some embodiments, the occurrence of different motion primitives may alter the visual effect, color, brightness, or persistence of the visual trace 202. For example, a fast sprint up the court may be visualized as an elongated thinner visual, whereas a sharp lateral cut may have a thicker, brighter, or more pronounced visual appearance. While FIG. 9 simply illustrates the visual traces 202, in some embodiments there may be corresponding, wearable-triggered audio effects that may be recorded and played back with the video. As such, a motion primitive that results in a prominent trace, such as may be caused by dunking a basketball or making a sharp cut, may also have an audio effect associated with it.

In still another embodiment, the visual traces may be scored with music that is stored in memory associated with the user's device 200, or accessible to the user's device 200 via a streaming media service/subscription. In this embodiment, the user's device may understand the timing and tempo of the motion and created visual output and may select an audio/music track that has a similar beat or rhythm. In instances where the available audio slightly mismatches the beat or timing of the motion, the user's device may be operative to select the closest possible audio and then modify the beat or tempo to match.

The use of electronic, motion-sensing apparel or footwear in the present manner enables a new form of expression and creativity that is not possible through other, more traditional electronic inputs. Each sport and each player within a sporting event may create their own unique auditory or visual experience that be unique to that athlete's style and performance. This experience may be broadcast to users either directly (e.g., via speakers or lights within the facility), or via one or more hand held devices that are in communication with the user console paired with the athlete's wearables. In a non-sporting sense, the present technology enables performers (both professional and those streaming on the interne at home) with a new means of digitally augmented expression, with their own movements being the direct trigger for an A/V experience.

Pre-set themes or genres may be used or applied in any of the above-referenced examples to introduce new suites of expression while altering the sounds or visual expressions according to a pre-defined rule. For example, an island/beach theme may alter the available sounds to a more calypso-themed suite of sounds and/or may alter the available colors and/or visual effects to ones within a blue/green/tan color palate.

Figure 10:
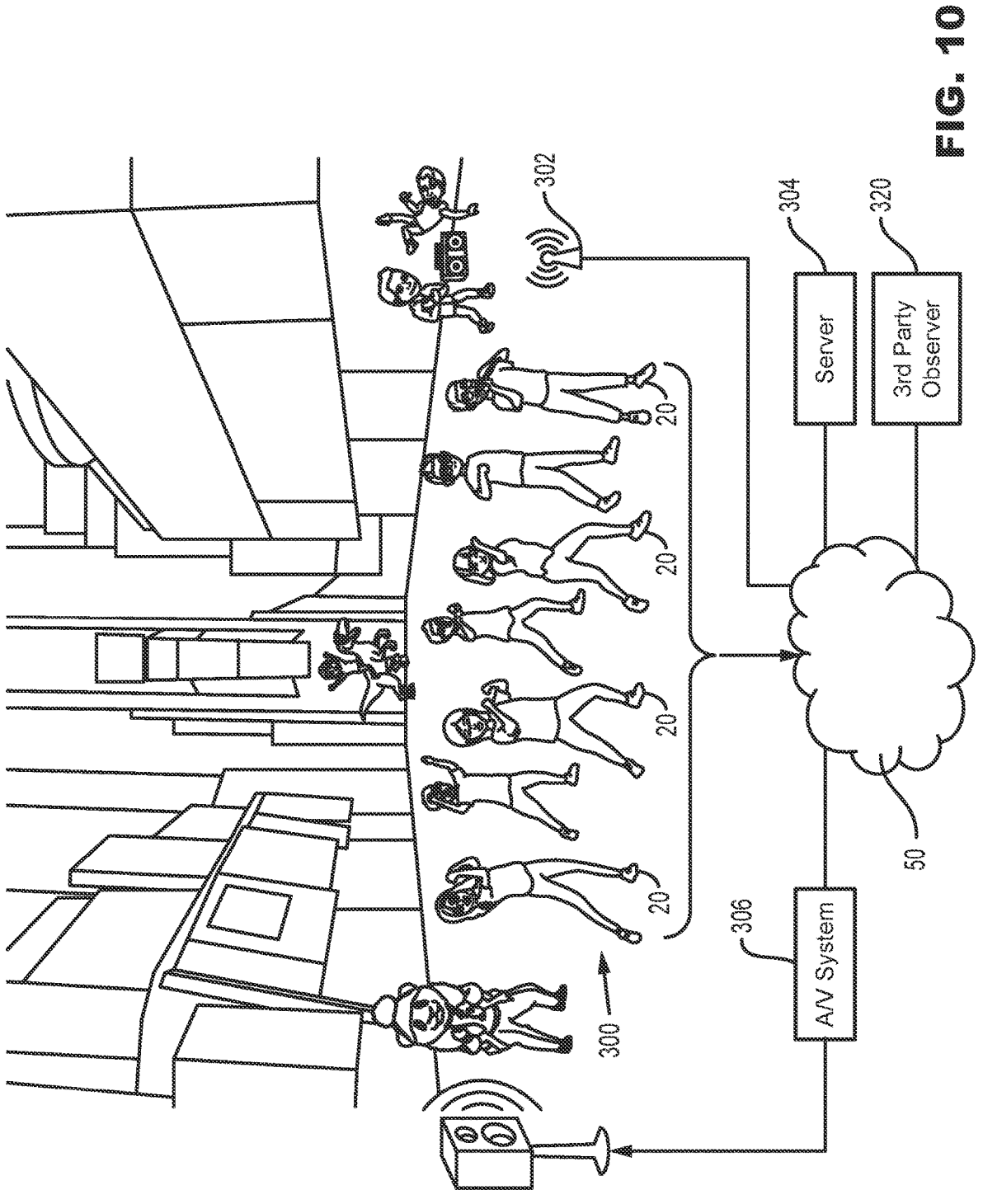
FIG. 10 is a schematic illustration of a flash mob with each participant having a wearable with location-based access to audio/visual output.

In one embodiment, such as shown in FIG. 10, access to or use of a particular correspondence table (or an associated theme) may be unlocked and/or made available only if the user device/wearable is present at a specific time and location. For example, members of a flash mob 300 may all gain usable access to a predefined A/V theme upon arriving at a park or city square where the flash mob is intended to perform. The user device/wearable 20 may understand its location, for example, through the use of GPS, RF triangulation, wifi network recognition, RF beacons 302, BLUETOOTH position tracking, or the like (generally, "location sensing means"). Upon arrival at the predetermined location (or within a predetermined distance thereof) at the predetermined time, any wearable 20 that is registered with a connected server 304 as being part of the group may then be configured to begin recognizing motion primitives of the user and/or to begin transmitting motion data to the distributed network 50. By requiring users to opt-in to the group, participation may be limited to only those who knowingly wish to become part of the group, while those who just happen to be at the right location at the right time would be excluded and/or prevented from unknowingly joining the group.

In the example of a flash mob, the wearable 20 worn by each user may have connectivity to a common distributed computing network (WAN, wireless LAN, etc), with each wearable being connected directly or through a smart phone, watch, or other connected device. The conversion from sensed motion primitives to a triggered response may occur either locally to each wearable 20, or more centrally on a networked server 304/data aggregation device. The collective user output may then be converted to an audio or visual output either via a local A/V system 306 (e.g., for playback by a local speaker 308 or visual effect device) or may be passed via the network to a third-party device 310 where it may be output as audio (via headphones or speakers) or displayed visually on a screen in augmented or mixed reality, in a similar spirit as shown in FIG. 9.

As noted above, in some embodiments, one or more visual effects may be triggered in response to the sensed motion primitive. To this end, FIGS. 11-14 schematically illustrate three embodiments of a wearable 20 that includes one or more integral light emitting elements 400 that may be triggered to outwardly project visible light in response to one or more detected motion/motion primitives (e.g., at the direction of a visual effect controller 48).

Figure 11:
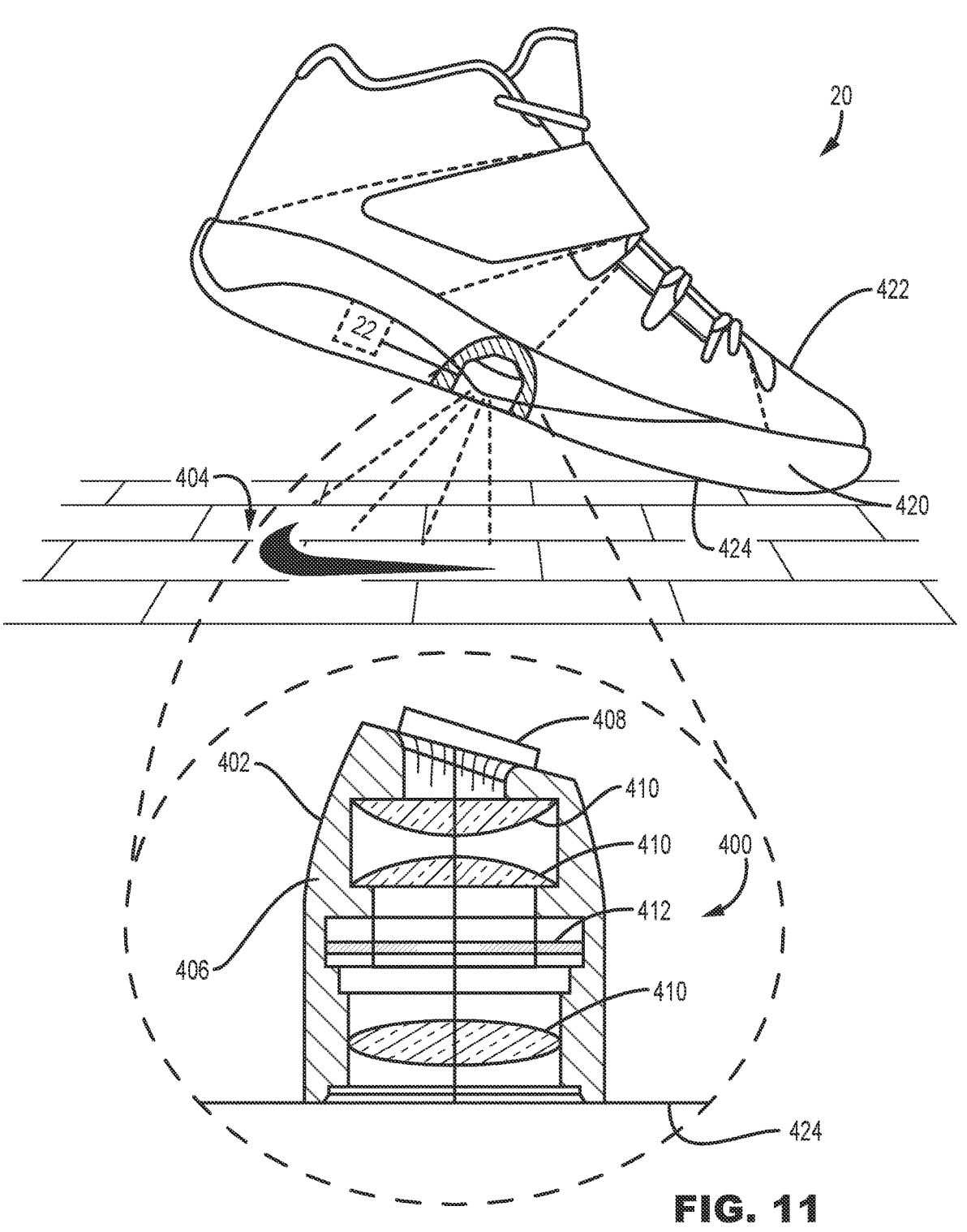
FIG. 11 is a schematic partial cross-sectional side view of a motion activated light projector provided within an article of footwear.

As schematically illustrated in FIG. 11, in one embodiment, the light emitting element 400 may be a projector 402 that is operative to cast a predetermined pattern of light on an adjacent surface 404, such as the ground. As specifically shown, the projector may include a housing 406, a light source 408 such as a light emitting diode (LED), one or more lenses 410 (e.g., one or more condensing lenses and/or objective lenses), and an optional slide or stencil 412. When used, the slide or stencil 412 may enable the projector 402 to project an image (e.g., logo, silhouette, or graphic) onto the surface 404 rather than simply just casting an ordinary ball of light. In one configuration, the projector 402 may be integrated into a midsole 420 of an article of footwear 422 and oriented such that it projects light through an outsole or ground-facing outsole surface 424. In other embodiments, instead of projecting light through the outsole or ground-facing outsole surface 424, the projector may be positioned/oriented to cast an image on the ground surface 404 next to the article of footwear 422. In such an embodiment, the projection 402 may be positioned on, or at least partially extending through a sidewall of the midsole.

In the configuration where the light emitting element 400 shines through the ground-facing outsole surface 424 of the article of footwear, the projected light would only be visible to surrounding observers only if the wearer of the article lifted their foot off the ground. To conserve power, in one configuration, the light emitting element 400 may be controlled to illuminate only when the article of footwear detects that it is in motion off of the ground, or when it may be detected that the foot has moved a sufficient distance away from the ground for the broadcast light to be visible to an observer (i.e., where position may be derived from sensed acceleration data). In still another embodiment, the light emitting element 400 may be controlled to illuminate only if the wearable 20/motion sensing circuit 22 senses an upward acceleration above a certain threshold. Such may indicate a jump, or a jump of a particular magnitude, and may further aid in ensuring a certain minimum duration for the illumination or that an ideal focal distance is achieved for the projector 402 to project an image of sufficient clarity.

Figure 12:
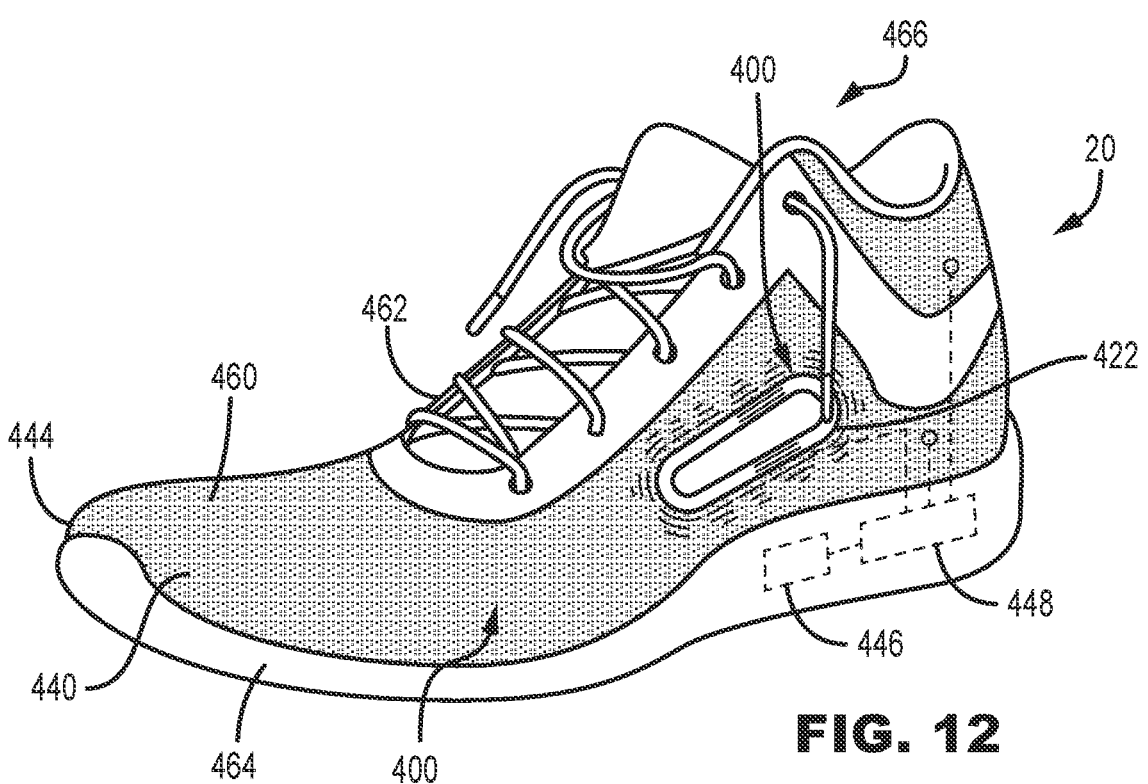
FIG. 12 is a schematic perspective view of an article of footwear with a plurality of light emitting elements.
Figure 13:
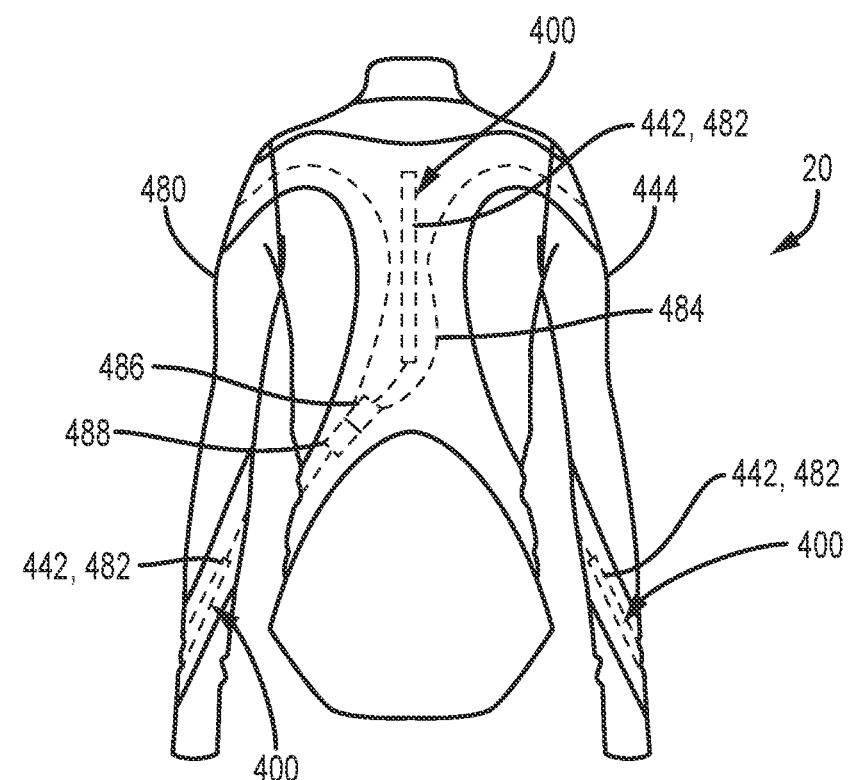
FIG. 13 is a schematic rear view of an article of apparel with a plurality of light emitting elements.

As shown in FIGS. 12-13, in some embodiments, the light emitting element 400 may be a lighted panel 440 and/or illuminated design element 442 that is provided on or otherwise integral with an article of footwear or apparel (i.e. illuminating article 444). In some embodiments, this illuminating article 444 may be the same as the wearable 20 described above, however in other embodiments, it may be distinct from the wearable 20 though in electrical communication (directly or indirectly) with the wearable 20. For example, the wearable 20 could be an article of footwear, while the illuminating article 444 could be a glove or shirt. The article 444 may further include a power source 446 and a controller 448 that is operative to modulate the electric power supplied from the power source 446 to the panel 440 and/or design element 442. In some embodiments, the controller 448 may be the visual effect controller 48 described above.

FIG. 12 generally illustrates the illuminating article 444 as an article of footwear 460 that includes an upper 462 coupled to a sole structure 464. The sole structure 464 extends between the foot and the ground when article 460 is worn. In different embodiments, sole structure 464 may include various cushioning components including a foamed polymeric midsole, one or more integrated fluid-filled chambers (e.g., airbags), a foamed insole, like. Additionally, in some embodiments, it may include one or more recesses or cavities to accommodate the power source 446, controller 448, and/or any other sensors or electronic components that may be used by the article 444.

The upper 462 may include a variety of provisions for receiving and covering a foot, as well as for securing the article 444 to the foot. The upper 462 includes an opening 466 that provides entry for the foot into an interior cavity of upper 462. Some embodiments may include fastening provisions, including, but not limited to: laces, cables, straps, buttons, zippers as well as any other provisions known in the art for fastening articles.

As generally illustrated in FIG. 12, in one embodiment, an outer wall of the upper 462 may include the lighted panel 440. The lighted panel 440 may include a plurality of different layers, with at least one being an electroluminescent layer (or EL panel). Exemplary EL panel technologies that could be used include, but are not limited to: light-emitting capacitor (LEC) panels, powder phosphor-based electroluminescent panels, and thin film electroluminescent materials. Additionally or alternatively, the lighted panel 440 may include one or more light emitting diodes or other illuminating elements that, when diffused, could illuminate an area of the panel. Additional embodiments and further details regarding an article 444 with a lighted panel 440 are described in, for example, U.S. Pat. No. 10,182,608, which is incorporated by reference in its entirety.

In some embodiments, the article of footwear 460 may include one or more illuminated design elements 442. These design elements 442 may include spotlighted features or discrete elements as opposed to more generally illuminated areas, such as the lighted panel 440. In some embodiments, however, there may be overlap between the two (i.e., a design element may be a panel-illuminated logo or accent). In this vein, the one or more illuminated design elements 442 may include illuminated logos or embellishments such as described in U.S. Pat. No. 8,056,269, illuminated straps such as described in U.S. Pat. No. 10,004,291, illuminated strands such as described in U.S. Pat. No. 8,813,395, and illuminated cavities or fluid-filled cushioning components such as described in U.S. Pat. No. 8,356,430 and US Patent Publication No. 2009/0158622, each of these references being incorporated by reference in their entirety.

While FIG. 12 illustrates the article 444 as an article of footwear, FIG. 13 generally illustrates the article 444 as an article of apparel/clothing 480, and more specifically as a shirt or jacket in an as-worn condition. In other embodiments, the article of apparel/clothing 480 may additionally or alternatively include other types of shirts (long sleeve, short sleeve, tank top, vest), pants, socks, body suit, hat, gloves, outerwear, and/or any other desired type of apparel. As shown, the article of apparel/clothing 480 includes an illuminated design element 442 that comprises a light array 482, a plurality of embedded conductive traces 484 a power source 446, and a controller 448. The light array 482 may comprise, for instance, a plurality of discrete visible light sources (e.g., LED, OLED, an electroluminescent material, and the like) arranged in, for instance, a single line of lights or two or more rows of lights. The light array 482 may also comprise a continuous line of lights using, for instance, a fiber optic light and/or an optical fiber. The light array 482 is configured to be, thin, bendable, and flexible so as to conform to body curvatures when the apparel item is worn. The light array 482 may be affixed to the apparel item using, for instance, a polymer layer such as a thermoplastic polyurethane (TPU) or a silicone-based polymer. Further details on exemplary illuminable articles of apparel/clothing are described in US Patent Application publication Nos 2019/0059461 and 2019/0200690, both references being incorporated by reference in their entirety.

In some configurations, the light emitting element 400 of FIGS. 12-13 may be used as one or more of the outputs of the user collaboration architectures shown in FIGS. 5-7. For example, in a collaborative visual or audio/visual composition, a plurality of users may each be wearing one or more illuminating articles 444 that each have one or more light emitting elements 400 provided thereon. Different motion primitives or combinations of motion primitives may then trigger the illumination of different ones of the light emitting elements 400, with color, luminosity, duration, and/or illumination pattern (e.g., solid, flashing, rapid flashing, scrolling, etc) being either pre-defined in response to the motion primitive, or else being a function of a magnitude of the primitive. For example, a sharper lateral cut may result in a brighter panel illumination than a less aggressive lateral cut (e.g., as measured by lateral acceleration magnitude or lateral jerk magnitude (da/dt)).

In one example, a body suit or jacket such as shown in FIG. 13 may be used by a stage performer who wants to add a visual flair to his/her performance. In another example, an illuminating article of apparel such as shown in FIGS. 12 and 13 may be used by a runner or cyclist to signal to others nearby. For example, a runner with a smartwatch wearable may raise a hand to signal to an oncoming vehicle. The wearable 20 may recognize the motion primitive associated with the hand raise, which may then trigger some of all of the light emitting elements 400 to illuminate. In one configuration, different hand motions may cause different illumination patterns. For example, extending the hand upward may cause a first set of lights to illuminate, while extending the hand outward may cause a second set of lights to illuminate.

When using the present technology to compose an audio/visual performance, it may be particularly challenging to stay on beat in the absence of an external rhythm. More specifically, in such a use case, the user may lack many of the external cues (e.g., a bass beat) that may otherwise be used to set rhythm/timing. This problem may be particularly evident in a collaborative group composition, which may have otherwise relied on the beat of a song to synchronize the tempo and rhythm of the performers.

Figure 14:
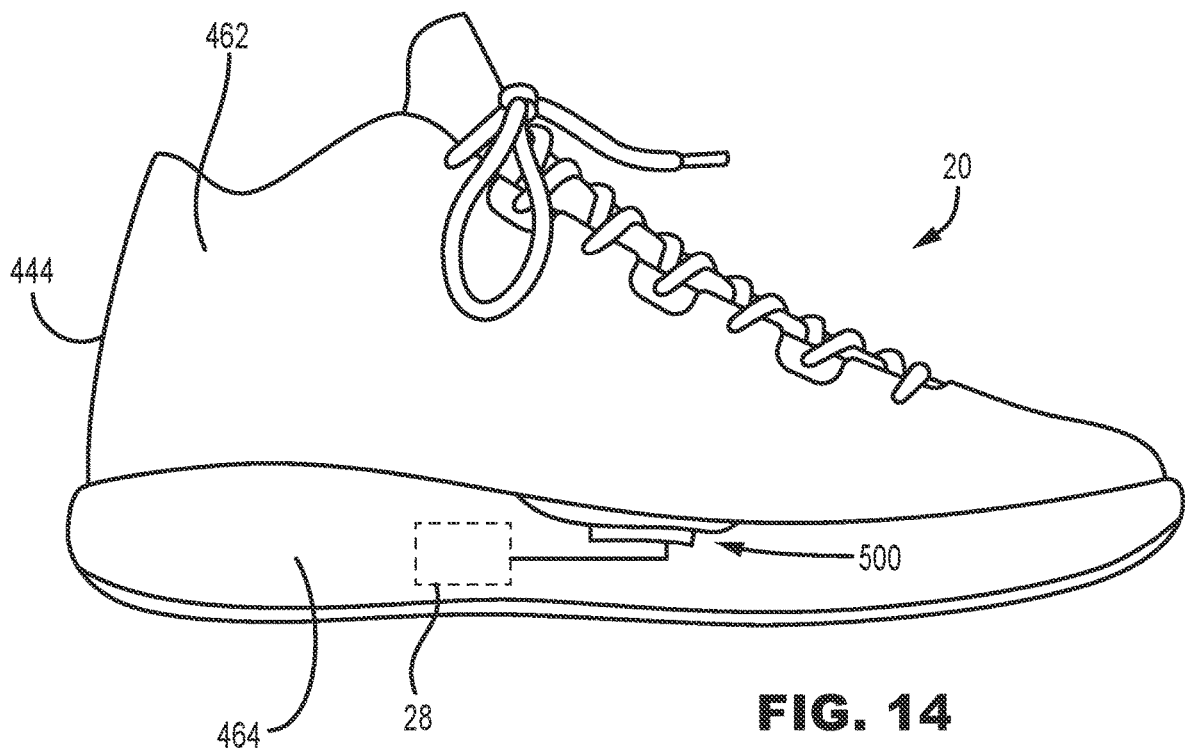
FIG. 14 is a schematic partial cross-sectional view of a vibration transducer provided within an article of footwear.

To aid the one or more users in beat tracking and/or staying synchronized with other collaborating individuals, the wearable 20 may include a vibration transducer 500 that is operative to transmit a tactile sensation to the body of the user. FIG. 14 schematically illustrates one embodiment of such a wearable device 20. In this embodiment, a vibration transducer 500 is provided within a sole structure 464 of an article of footwear 444. In other embodiments, however, the vibration transducer 500 may be provided with the upper 462 of the article of footwear 444, or on/with an article of apparel such as a watch, sleeve, shirt, pants, shorts, glove, hat, or any other garment or accessory in contact with the user's body.

The vibration transducer 500 may operate at the direction of the processor 28 to convey a beat or other tactile timing signal to the user. In multi-user environment, this timing signal could then be synchronized across each of a plurality of users to aid in creating a properly timed composition (e.g., during a flash mob). In one configuration, the vibration transmitted to the user by the vibration transducer 500 may be a switched or compound vibration that comprises a tactile waveform that is switched according to a specified beat. The tactile waveform may be a vibration having a frequency in the range of, for example and without limitation, about 100 Hz to about 300 Hz, or in the range of about 140 Hz to about 210 Hz, or in the range of about 230 Hz to about 260 Hz. This vibration may be selected so that the user may most easily perceive the notification from the vibration transducer 500 when such a notification is provided.

The intended beat of the song or composition may be represented by a periodic transmission of the tactile waveform with the periodic transmission having a duty cycle of less than about 50%, or more preferably less than about 30%, or in the range of about 5% to about 25%. The beat may have a transmission frequency of between about 0.1 Hz and about 3 Hz. More appropriately, if measured in beats per minute (BPM), the switched beat may transmit the tactile waveform approximately 30 to about 160 discrete times per minute. In some embodiments, every beat of a composition need not be expressed. Rather, only certain synchronizing beats might be expressed (e.g., one of 4 or one of 8 consecutive beats in a composition). Regardless of the specific frequency of the beat, the tactile waveform may represent a short-duration buzz, whereas the beat is the timing on which those short-duration buzzes occur.

In some embodiments, instead of a periodic vibration being conveyed by a vibration transducer, a similar beat may be conveyed by constricting or tightening a portion of the wearable 20 (or an article of footwear or apparel in communication with the wearable) about the body of the user. To accomplish the constriction, the wearable 20 (or other article) may include one or more tensioning mechanisms that are operative to tension one or more fibers, cords, laces, closure mechanisms, or other fit-adjusting aspects of the article in a tangential direction around a portion of the wearers body. In doing so, the tension in the article may then urge the article to constrict or reduce in size in a radial dimension, which would impart a compressive force against the wearer. Articles that may be particularly adapted for such a compression include shoes (i.e., adaptive lace tensioning), compression sleeves/garments, and watches/bracelets.

In some embodiments, the tensioning mechanism may include a motor that is operative to spool/unspool a tensile fiber embedded within the article in response to an actuation signal. In other embodiments, the tensioning mechanism may include one or more linear actuators, fast response active materials (e.g., piezo actuators), or micro-electromechanical systems (MEMS). The tensioning mechanism may be configured to respond to a provided switched beat to periodically induce a momentary compression against the user's foot/body. Additional descriptions of the tensioning mechanism in a footwear context are provided in U.S. Pat. No. 10,448,707, U.S. Patent Publications 2018/0199673, 2017/0265583, and/or U.S. application Ser. No. 16/694,306, each of which is incorporated by reference in its entirety.

Figures 15, 16:
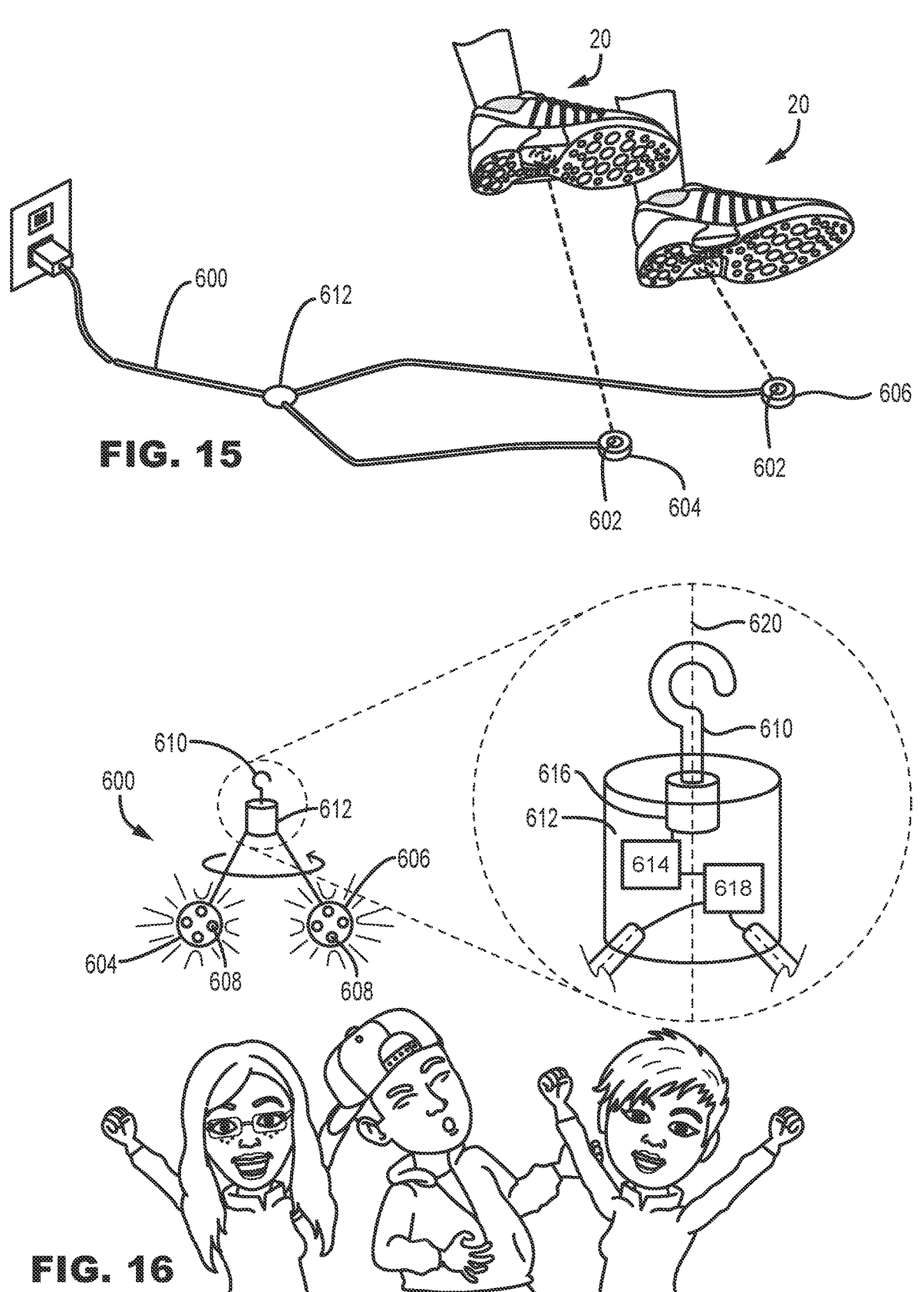
FIG. 15 is a schematic side view of an inductive charger being used to charge a plurality of wearables.
FIG. 16 is a schematic side view of the inductive charger of FIG. 15 being used as a party light.

FIG. 15 schematically illustrates a charging device 600 that may be used with a wearable 20 such as described above. As may be appreciated, each wearable 20 may include a battery that requires periodic recharging in order to maintain the device's ability to perform the above-described functions. To provide a measure of waterproofing, the charging device 600 may by an inductive charging device that comprises one or more inductive coils 602. Each inductive coil 602 may be operative to magnetically induce a charging current within the wearable 20 when the coil 602 is energized with an alternating current waveform and is brought into close proximity to the wearable 20. In the case of an article of footwear, two inductive charging pucks 604, 606 may be required (i.e., one for each shoe), where each puck 604, 606 includes an energizable inductive coil 602. An example charging device is described in US 2017/0150773, which is incorporated by reference in its entirety.

As schematically shown in FIG. 16, in some embodiments, the charging device 600 may further include the ability to double as a disco-ball or party light. More specifically, each charging puck 604, 606 may include a plurality of lighted elements 608 (e.g., LEDs) that are operative to project light of varying intensity and/or color. Further, the charging device 600 may include a mounting feature 610, such as a hook or stand that may support the charging device in a posture that is suitable for partying. The mounting feature 610 may be integral with or may otherwise attach to a central hub 612 from which each of the charging pucks 604, 606 extend. The central hub 612 may include an energy storage device 614, a movement mechanism 616, and/or a lighting controller 618, while also providing suitable strain relief for any wires extending to the charging pucks.

When used as a party light, the energy storage device 614 (e.g., a battery) may supply the electrical power needed to illuminate the lighted elements 608 as well as the power required to facilitate any external communications or drive any powered aspects of the movement mechanism 616. The energy storage device 614 may be charged concurrently with the wearable 20 when the charging device is plugged in to an AC power source. Conversely, the energy storage device 614 may expend energy when the charging device 600 is operated as a party light.

The movement mechanism 616 may be configured to induce movement of the charging pucks 604, 606 and/or lighted elements 608 to provide a visual effect similar to a disco ball or other moving spotlight. The movement mechanism may include, for example, one or more motors, wind-up/spring driven mechanisms, or articulating mirrors/lenses. The movement mechanism 616 may generally create a rotation or oscillation of at least a portion of the charging puck or lighted element to alter how the light is projected. As schematically shown in FIG. 16, in one particular embodiment, the movement mechanism 616 may cause the central hub 612 to rotate relative to the mounting feature 610, which may in-turn cause the charging pucks 604, 606 to rotate about a central axis 620.

The lighting controller 618 may be responsible for illuminating the one or more lighted elements 608 to create the visual effect. In one configuration, the lighting controller 618 may simply illuminate the lighted elements 608 in a repeating pattern that may be pre-programed and/or user controlled. For example, a predefined collection of illumination patterns and sequences may be preprogrammed into the lighting controller at the time of manufacture. The user may then select the desired pattern/sequence, for example, by clicking a button on the hub 612 or by selecting it via a connected wireless device (e.g., remote, smartphone, computer, etc).

In another configuration, the lighting controller 618 may illuminate the lighted elements 608 in response to audio that may be sensed via an integrated or connected microphone. The lighting controller may, for example, pulse lights in response to a sensed low-frequency beat, or may alter lighting patterns or colors according to sensed pitch or frequency. In one configuration, the microphone may be integrated into a connected wireless device, which may transmit either raw sensed audio data, audio summary data (e.g., beat or pitch data), or program commands based on sensed raw audio or audio summary data.

In still another configuration, the lighting controller 618 may receive a digital signal from the wearable 20 and may illuminate the lighted elements 608 on the basis of one or more sensed motion primitives, as discussed above. As such, the lighting controller 618 may include, or may be in communication with the visual effect controller 48 and the charging device 600 may serve as means for displaying the visual expression of the user's movement (or else may complement the user's visual movement). In this manner, it may be possible for the lighted elements 608 to synchronize their movement and or flashing with the rhythmic movement of one or more people dancing near the light.

Figure 17:
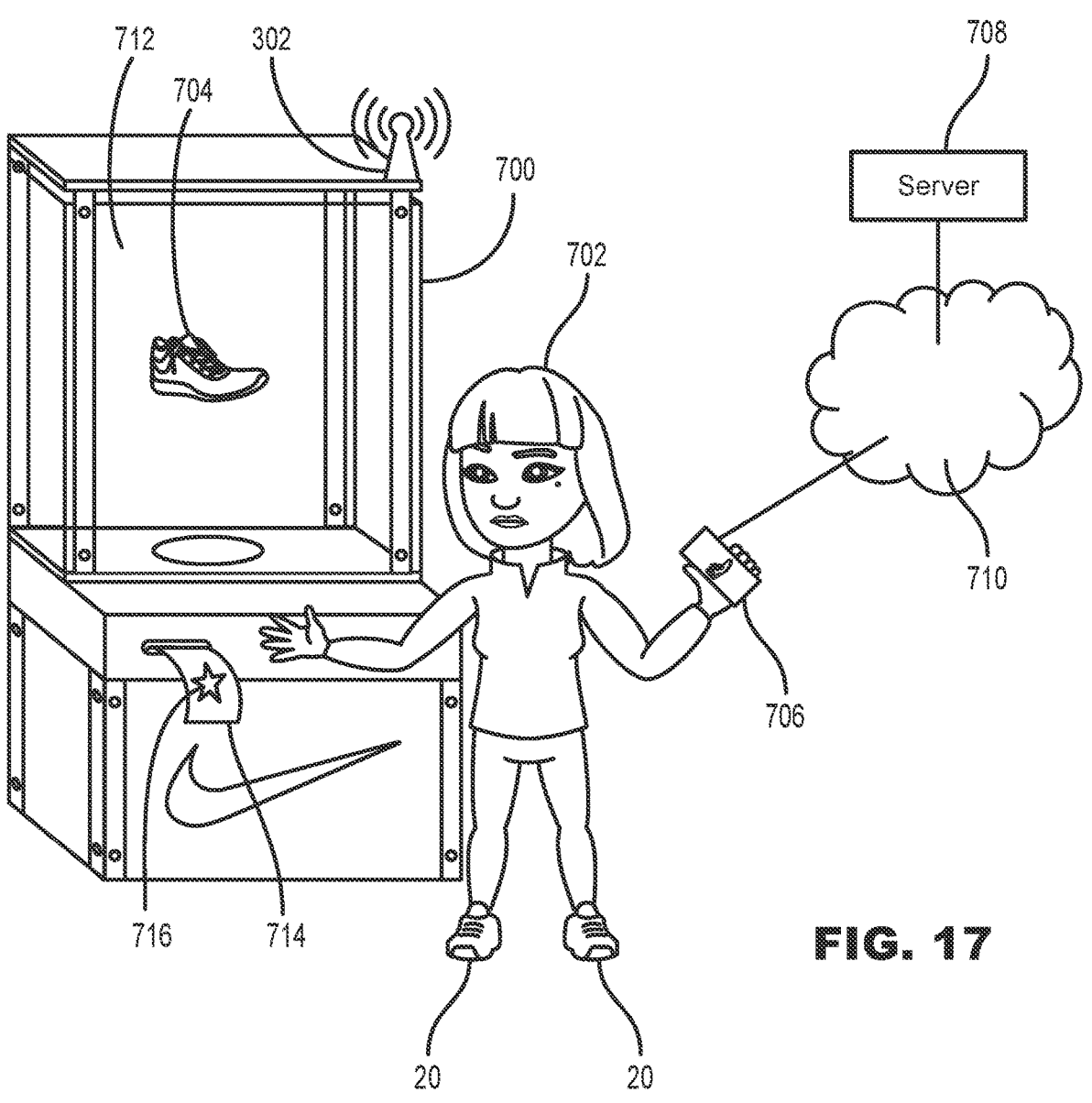
FIG. 17 is a schematic perspective view of an interactive retail kiosk.

In some embodiments, instead of triggering the playback of an audio sample or a visual effect in response to the identified at least one motion primitive, the motion primitive may serve as the input to an external game. For example, in some embodiments, the shoe may serve as the input to a dance-based video game where a sequence of movements are displayed on a video display, and a user must do his or her best in replicating the movements to achieve a high score. In another embodiment, such as shown in FIG. 17, the game may be a retail-centric game that requires the user to perform one or more sequences of movement to acquire an unlock code, token, pass, authorization, or chance to acquire a retail product or digital collectible. In some embodiments, the retail product or digital collectible may be a limited release retail product, a digital representation of a retail product, a cryptographically secured digital asset such as described in U.S. patent application Ser. No. 15/931,764 and/or Ser. No. 16/707,720, both of which are incorporated by reference in their entirety, or some other item of limited or constrained supply.

FIG. 17 generally illustrates an interactive retail kiosk 700 that requires active user engagement in order for the user 702 to acquire a retail product 704, a digital representation of a retail product, an unlock code or portion of an unlock code for acquiring a physical or digital retail product, or a digital recognition of an accomplishment (e.g., a virtual badge that may be shared on social media).

Figure 18:
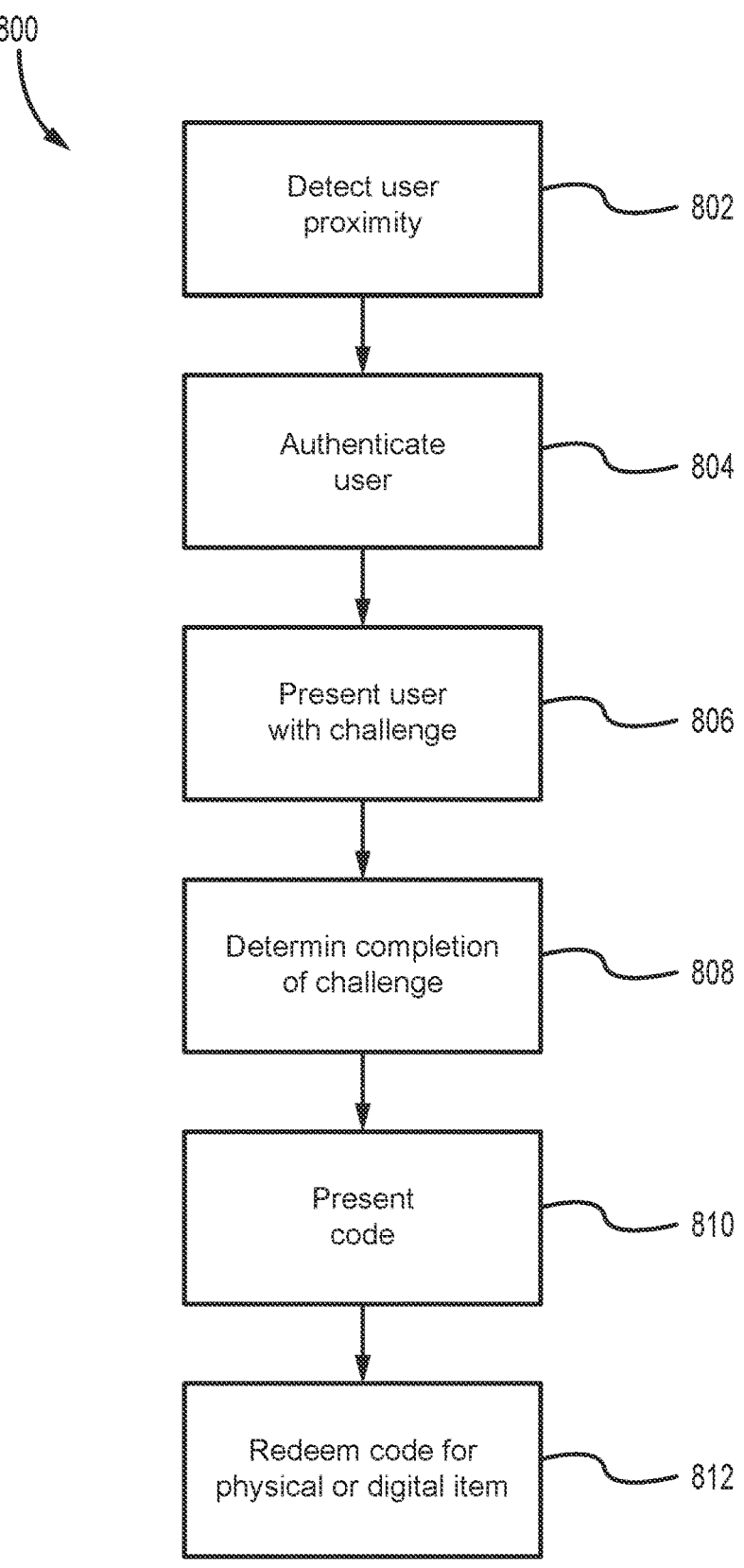
FIG. 18 is a schematic flow diagram of a method of acquiring a physical or electronic object or code such as with the interactive retail kiosk of FIG. 17.

FIG. 18 schematically illustrates a method 800 of acquiring a physical or electronic object or code, such as may be performed with the interactive retail kiosk 700 of FIG. 17. As shown, the method may begin by recognizing the presence of a user 702 within a predefined physical proximity of the kiosk 700 (at 802). In one configuration, the kiosk 700 may include a camera, an RFID reader, a pressure mat provided on the floor next to the kiosk 700, or a button that a user may press to alert the system to the user's proximity. In another configuration, the user 702 may possess a wireless computing device 706 that is in wireless digital communication with a server node 708 via a communication network 710. The wireless computing device 706 may possess a means for recognizing the location of the user, such as a GPS receiver, a wireless communication component that can recognize the device's proximity to a wireless beacon 302 or local area network, or a camera that can perceive and recognize visual aspects or digital codes within the surrounding environment. Once the location of the user is recognized, an application running on the device may transmit an indication of the user's relative or absolute location near the kiosk 700 to the server node 708, which may initialize the game.

The wireless computing device 706 may further include the ability to authenticate a user's identity, such as by including an application that requires the user to enter a password, to present an identifying biometric feature (e.g., fingerprint or facial recognition), or to otherwise be securely logged in to the application. At step 804, the user's wireless computing device 706 may authenticate the user's identity and location as being physically present within a predefined proximity or geofence of the kiosk 700.

Once the user is authenticated and recognized in proximity to the kiosk 700, the server 708 may present the user with a particular challenge (at 806). In one configuration, the challenge may be presented to the user 702 via a display 712 that is coupled to, or in communication with the kiosk 700. In another embodiment, the challenge may be presented to the user via the communication network 710 and a display provided on their wireless computing device 706. In general, the challenge may comprise a series of movements, motions, or actions that the user is asked to perform in sequence. For example, the challenge may comprise a dance sequence, a set of exercises such as jumping jacks, lunges, burpees, high knees, kicks, or a series of yoga poses.

Once the user is presented with the challenge at 806, the user 702 may perform the requested physical activity and the server node 708 may determine that the challenge has been successfully completed (at 808). This determination may come either from direct observation (e.g., via a camera or pressure mat provided with the kiosk 700) or by receipt of a digital indication that the challenge has been performed. In one configuration, the received digital indication may be provided by a wearable 20 as a transmitted sequence of motion primitives, or else as a simple indication that the wearable 20 has detected a sequence of motion primitives that match or closely approximate what would be expected during successful completion of the challenge.

Following a determination that the user 702 has successfully completed the challenge (at 808), the kiosk 700 may then present the user with a code (at 810) that may be redeemed for a retail product (at 812), or combined with other codes to be collectively redeemed for a retail product (or limited release digital object). As generally shown in FIG. 17, in one embodiment, kiosk 700 may present the user 702 with a printed receipt 714 that has a machine readable code 716 printed on it. In another embodiment, the kiosk 700 may digitally transmit the code 716 to the user's device 706 or to a user account that had been authenticated by the server 708 prior to the issuance of the challenge. Once transmitted, the code 716 may be maintained within a digital locker/ storage or within a cold storage digital wallet such that the user can access the code at a future time.

In one embodiment, the kiosk 700 may be located at a retail store and the code may be handed to retail associate or entered into an internet interface to redeem a retail product of similar style or design as the product 704 displayed in the kiosk 700. In another embodiment, a user may need to acquire multiple codes, each from a different kiosk, to qualify for the product. In this multi-kiosk scenario, the plurality of kiosks may be distributed over a geographic area and/or at a plurality of retail stores, and the user may be required to search them out, such as described in U.S. Patent Publication 2019/0213619 and U.S. patent application Ser. No. 16/874,944, which are incorporated by reference in their entirety. In this configuration, the user may be sent on a scavenger hunt to accumulate the codes required for the product unlock. As generally discussed in U.S. patent application Ser. No. 16/874,944, in one embodiment, the user may be guided to the next kiosk through the use of turn by turn navigation built into the shoes (e.g., by selectively tensioning the laces, or through selective actuation of the haptic transducer illustrated in FIG. 14).

While the retail kiosk 700 is illustrated in FIG. 17 as physical product display, in other embodiments, it may simply be a non-retail display such as an oversized logo, sign, or other marker that may or may not have direct interactive capabilities. In some embodiments, the kiosk 700 may be a virtual kiosk (i.e., viewable with a suitable wireless computing device in an augmented or mixed reality context), or may be a virtual waypoint or location, such as a geofenced area.

Figure 19:
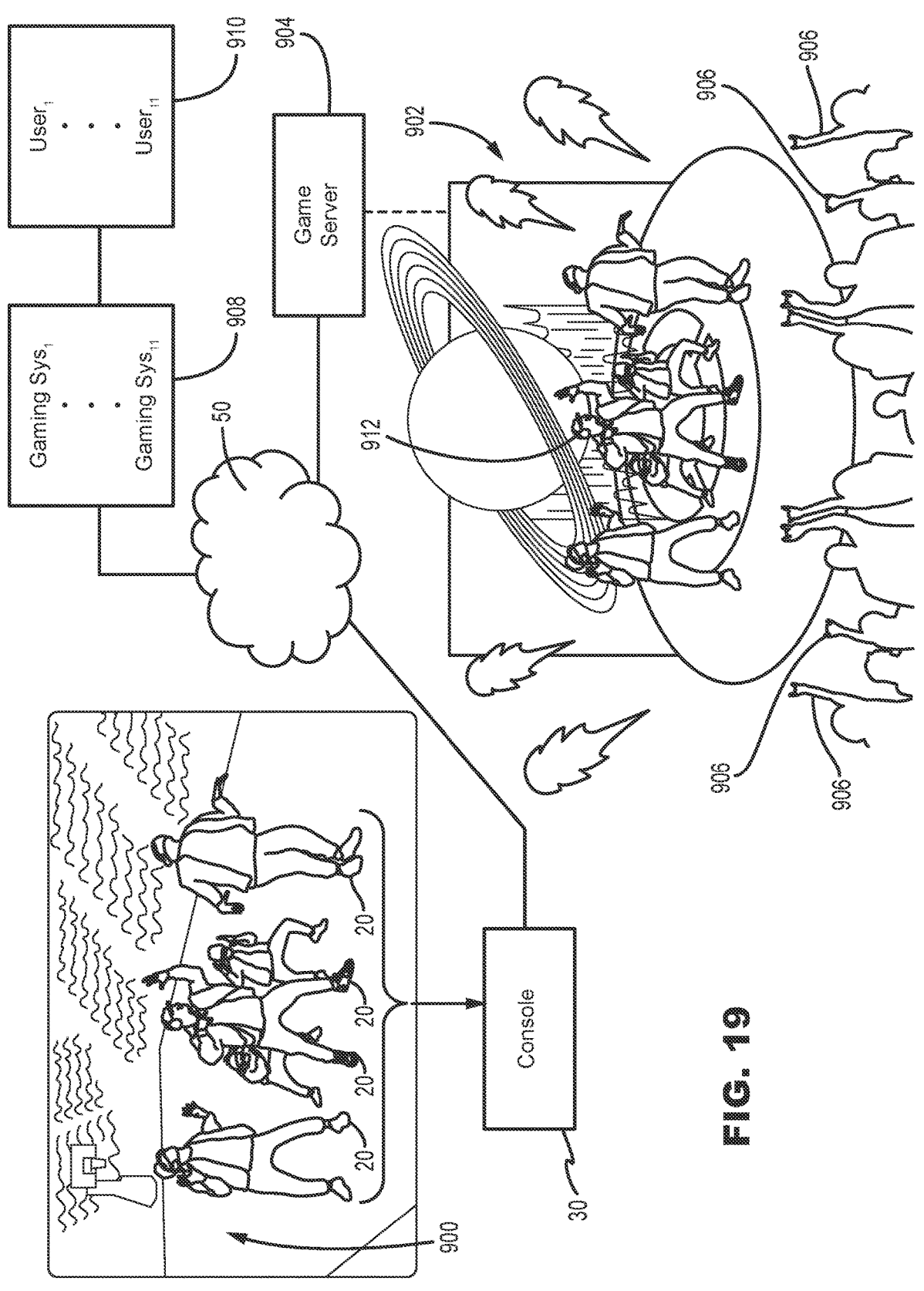
FIG. 19 is a schematic illustration of a group of performing artists using connected wearables to influence a performance within a hosted virtual world.
Figure 20:
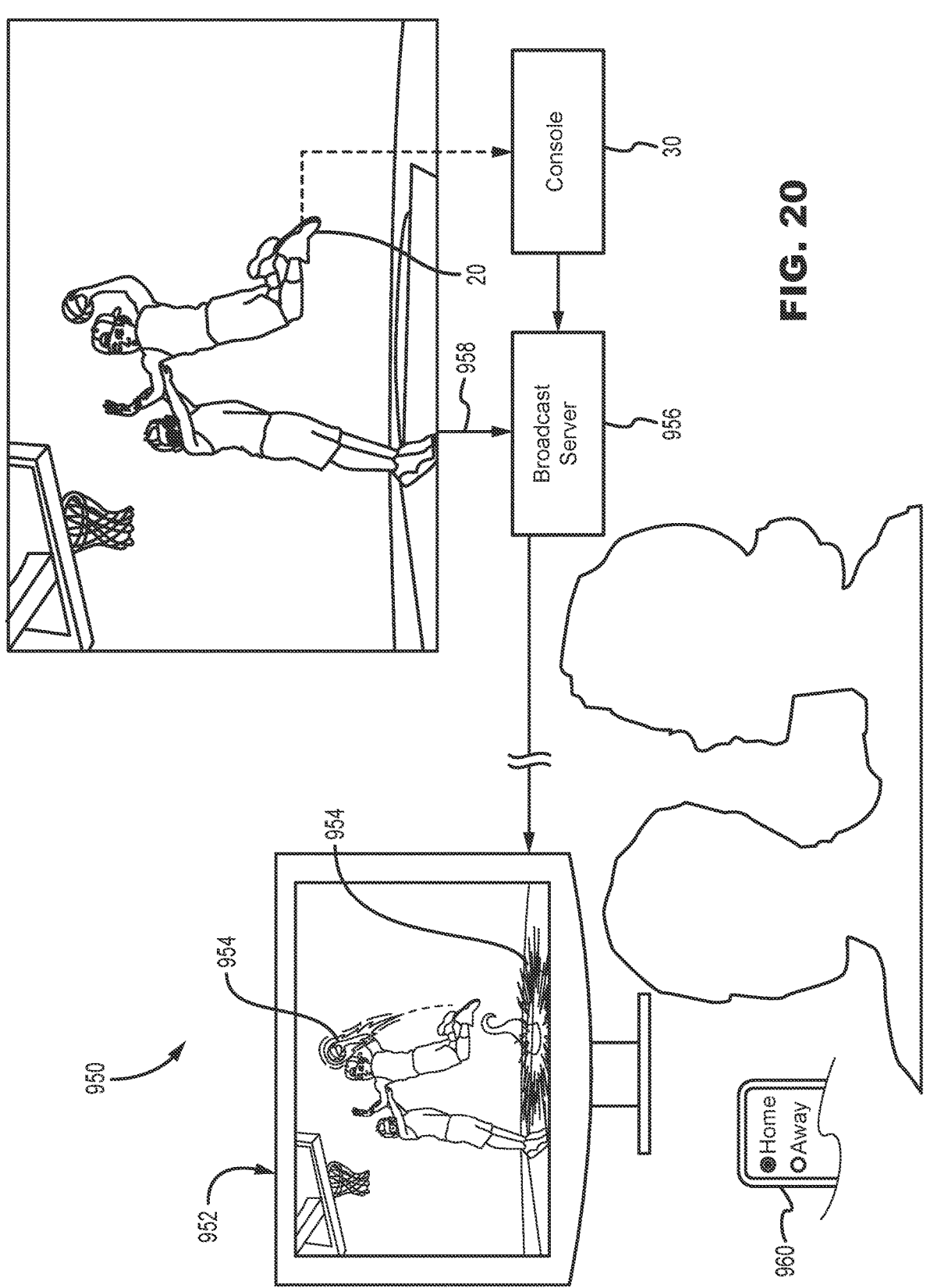
FIG. 20 is a schematic illustration of a wearable being used to augment a live video broadcast.

While most of the disclosure provided above has been primarily focused on creating audio and/or visual effects within a live environment, similar experiences may also be created within a virtual world (e.g., as shown in FIG. 19) or used to augment a video broadcast of a live event (e.g., as shown in FIG. 20).

Referring to FIG. 19, it is becoming increasingly more common for musical artists 900 to broadcast live concert performances within online virtual environments. Such a virtual environment 902 may be hosted and/or maintained by a game server 904 that is connected to a distributed computing network 50 such as the internet. A plurality of users may interact with the virtual environment and with each other by way of unique, user-controlled avatars 906 within the environment 902. During gameplay, each avatar 906 may respond to respective motion/action commands that are made by web-enabled computing devices 908 controlled by the different respective users 910. Each user 908 may experience a first or third person perspective view from/of their avatar 906 within the virtual environment 902 via a display associated with their respective web-enabled computing device 908. A popular example of such an environment exists through the game FORTNITE® developed by Epic Games.

In the embodiment shown in FIG. 19, much like the embodiments described above, a user console 30 may receive a data stream from a wearable 20 provided on the body of the musical performer 900. The user console 30 may rely on a similar motion correspondence table 110 to trigger the playback of an audio sample or visual effect that has been previously associated with that motion primitive. The main difference, however, is that the triggered audio sample or visual effect occurs solely within the virtual environment 902. For example, a lateral swish of the performer's foot may cause the sky within the environment to change color, a stomp of the user's foot may set off virtual pyrotechnics, and a downward thrust of a user's first may cause the playback of a strong percussion/kick drum that may be accompanied by, for example, a visual shockwave emanating outward from the performer's avatar 912. Additionally, instead of the motion primitives only being used to control sound or visual effects, the motion primitives sensed by the performer's wearable(s) may also be used to control or alter some or all of the motion or action of the performer's avatar 912 within the virtual environment 902.

While FIG. 19 utilizes the wearable 20 to control aspects of a virtual world, the system 950 shown in FIG. 20 is operative to use sensed motion to augment one or more aspects of a live video broadcast. In the context of a sporting event, a portion of an athlete's uniform may comprise a wearable 20 that is operative to detect or extract one or more motion primitives from the wearer's motion/activity. If the athlete executes a predefined move or series of moves, the visual broadcast 952 (television, cable, virtual reality, interne stream, etc) of the sporting event may then be augmented/altered with one or more visual effects 954 to emphasize or accentuate the athlete's action. For example, in a basketball game if an athlete were to dunk a ball with a threshold amount of force or leaping strength, upon landing on the ground, a broadcast system 956 may overlay the video feed 958 with a graphic of an explosion emanating from the athlete on the court surface itself. In another example, if a basketball player were to execute a signature crossover move, the sequence of actions may cause the broadcast system 956 to graphicly alter the perceived contours of the floor within the video feed 958— as if the athlete's plant foot was wrinkling the court surface. In doing so, this use of the present technology infuses aspects of embellished or cartoonish video games (e.g. similar to NBA JAM, produced by Electronic Arts Inc.) into live action sports while being triggered by the directly sensed motion of the athletes themselves (and not a by a third party visual observer).

In some embodiments, in addition to movement triggers, the generation of the visual effect may be further conditioned upon external factors, such as timing within a game, recent scoring activity, or the relative positioning of other players on the court/field. Furthermore, in some embodiments the existence, nature, or color of the effect may vary based on one or more preferences or attributes provided by the viewing user (i.e., via the user's respective web-enabled computing device 960). In such an embodiment, the user may first pre-select a favorite team or player, which may dynamically assign different motion correspondence tables to different players/teams. During the video broadcast, the pre-selected favorite team or player may then be augmented by a first set of sound/graphics, whereas other players (and in particular opposing players/teams) may be augmented by a second set of sound/graphics. The difference in in treatment between the designated favorite player/team and the opponent may have the effect of casting the pre-selected favorite player as the hero and casting the opposing player/team as the villain. This may be accomplished, for example, through the use of differing color palates, differing graphics, and/or differing sound effects.

Much like the enhanced sports broadcast 952, the visual effects ported into a virtual environment 902, such as shown in FIG. 19, may be different depending on one or more attributes or preferences of a user within that world. For example, the apparel/skin worn by a user's avatar may unlock certain color schemes or visual effects. Similarly, the level or experience of a user's avatar may also unlock different visual or audio effects. This may occur, for example, by either applying an entirely different correspondence table, or by making aspects of the correspondence table conditional upon certain criteria.

In addition to simply changing a visual or audio effect, it may also be possible for the output of the correspondence table to be transmitted to the user in the form of one or more haptic signals. Each haptic signal may direct a haptic device on the body of the user to provide a tactile response. These tactile responses may be in the form of a vibration or constriction of an article of footwear or apparel disposed on the user, and may be synchronized with one or more of the visual or audio effects. In this manner, the present technology may come by multiple senses to provide a more immersive user experience. In one embodiment, the haptic signal may further attempt to convey or impart one or more tactile sensations that may resemble those being experienced by the live athlete.

Various features and methods of operation of the presently described technology are set forth in the following clauses:

Clause 1. A system for dynamic movement scoring comprising: an article of footwear or apparel comprising at least one accelerometer or inertial measurement unit operative to monitor spatial motion of at least a portion of the article of footwear or apparel, and to generate a data stream indicative of the monitored spatial motion; a processor in networked wireless communication with the article of footwear or apparel, the processor configured to: receive the data stream from the article of footwear or apparel; identify at least one motion primitive from the received data stream; compare the at least one identified motion primitive to a predefined, ordered number of motion primitives; determine, an accuracy metric representing a correspondence between the monitored spatial motion of the article of footwear or apparel and the ordered number of motion primitives; and display the accuracy metric to the user via a display device.

Clause 2. The system of clause 1, wherein the processor is in digital communication with a distributed computing network, the processor further configured to: receive a challenge from the distributed computing network, the challenge comprising the ordered list of motion primitives; and display the challenge to a user via a display device.

Clause 3. The system of clause 2, wherein the challenge is received from a second user on the distributed computing network.

Clause 4. The system of clause 3, wherein the processor is further configured to receive an accuracy metric from the second user and to display it to the user via the display device.

Clause 5. The system of clause 1, wherein the processor is in digital communication with a distributed computing network; the processor further configured to transmit the accuracy metric to a server on the distributed computing network.

Clause 6. The system of clause 1, wherein the ordered number of motion primitives form a choreographed dance.

Clause 7 The system of clause 6, wherein the article of footwear or apparel further comprises a haptic transducer operative to transmit a tactile sensation to the body of the user; and wherein the processor is further configured to cause the haptic transducer to convey a beat or tactile timing signal to the user.

Clause 8. The system of clause 7, wherein the haptic transducer includes a motor operative to selectively and periodically tension at least one lace or closure mechanism of the article.

Clause 9. The system of clause 1, wherein the processor is further configured to trigger the playback of an audio sample or a visual effect in response to the identified at least one motion primitive.

Clause 10. The system of clause 9, wherein the identified at least one motion primitive includes a first motion primitive and a second motion primitive, and the audio sample or visual effect is a first audio sample or first visual effect and is triggered in response to the first motion primitive; and the processor further configured to: trigger the playback of a second audio sample or a second visual effect in response to the second identified motion primitive; and wherein the first audio sample or first visual effect is different than the second audio sample or second visual effect.

Clause 11. The system of clause 9, further comprising a user input device and a display in communication with the processor, and further wherein the processor is further configured to: maintain a library of a plurality of audio samples; associate, on the basis of a received input from the user input device, a selected audio sample from the plurality of audio samples with a predefined motion primitive; match the identified motion primitive with the predefined motion primitive; and wherein the triggering of the playback of the audio sample or the visual effect in response to the identified motion primitive comprises outputting the selected audio sample in response to the matching of the identified motion primitive with the predefined motion primitive.

Clause 12. The system of clause 1, wherein the processor is further configured to alter a behavior or motion of an avatar in a virtual environment on the basis of the received data stream.

Clause 13. A method of dynamic movement scoring comprising: receiving a data stream from an article of footwear or apparel, the received data stream being representative of a spatial motion of the article; identifying a plurality of motion primitives from the received data stream; comparing the at least one identified motion primitive to a predefined, ordered number of motion primitives; determining, an accuracy metric representing a correspondence between the monitored spatial motion of the article of footwear or apparel and the ordered number of motion primitives; and displaying the accuracy metric to the user via a display device.

Clause 14. The method of clause 13, further comprising: receiving a challenge from a distributed computing network, the challenge comprising the ordered number of motion primitives; displaying the challenge to a user via the display device.

Clause 15. The method of clause 14, further comprising transmitting the challenge to a second user on the distributed network.

Clause 16. The method of clause 13, further comprising transmitting the accuracy metric to a server on a distributed computing network.

Clause 17. The method of clause 13, further comprising triggering the playback of an audio sample or a visual effect in response to each of the identified motion primitives.

Clause 18. The method of clause 17, wherein triggering the visual effect comprises illuminating at least one light on the article of footwear or apparel.

The invention claimed is:

1. A method of controlling or augmenting a virtual reality environment or a live video broadcast according to sensed real time motion of a subject, the method comprising:
  receiving, from an accelerometer or inertial measurement unit provided on an article of footwear or apparel worn by the subject, a data stream indicative of a monitored spatial motion of the article of footwear or apparel;
  identifying at least one motion primitive from the received data stream, wherein the motion primitive is a discrete motion of the article of footwear or apparel or a predefined ordered sequence of such discrete motions, the discrete motion comprising one of translation, rotation, acceleration, jerk, impact, or periodic translation;
  augmenting the virtual reality (VR) environment or the live video broadcast with a visual effect in response to the identified motion primitive, wherein the visual effect is displayed at a location corresponding to the subject;
  transmitting a view of the VR environment or the live video broadcast to a viewer for display on a display device; and
  wherein the transmitted view of the VR environment or live video broadcast contains the visual effect; and
  wherein the visual effect includes a virtual pyrotechnics, or a graphic emanating from the subject within the live video broadcast.

2. The method of claim 1, wherein the VR environment or the live video broadcast is a VR environment; and
  wherein the VR environment includes a plurality of avatars including at least an avatar of the subject and an avatar of the viewer.

3. The method of claim 2, wherein the visual effect includes a motion or action of the avatar of the subject.

4. The method of claim 1, wherein the augmented VR environment or live video broadcast is a video broadcast of a sporting event.

5. The method of claim 4, wherein the subject is present within the video broadcast.

6. The method of claim 5, wherein the visual effect is a graphic emanating from the subject within the video broadcast.

7. The method of claim 6, further comprising receiving an indication of a preference or attribute of the viewer; and
  altering the existence, nature, or color of the visual effect according to the preference or attribute of the viewer.

8. The method of claim 4, further comprising receiving an indication of one or more external triggers; and wherein the existence of the visual effect is further conditioned on the one or more external triggers being present.

9. The method of claim 8, wherein the one or more external triggers comprise a game time of the sporting event, recent scoring activity within the sporting event, or relative positioning of other players within the sporting event.

10. The method of claim 1, further comprising:

maintaining a correspondence table comprising a plurality of video effects, each video effect corresponding to a different predefined motion primitive or series of predefined motion primitives;

matching the identified motion primitive with one of the predefined motion primitives within the correspondence table; and wherein the augmenting of the VR environment or live video broadcast with the visual effect comprises selecting the visual effect from the correspondence table that corresponds to the matched predefined motion primitives and overlaying the selected visual effect on the VR environment or the live video broadcast.

11. The method of claim 10, further comprising selecting the correspondence table from a plurality of correspondence tables according to an attribute or preference of the viewer.

\*    \*    \*    \*    \*